United States Patent
Hellenkamp

(10) Patent No.: US 7,166,117 B2
(45) Date of Patent: *Jan. 23, 2007

(54) AUTOMATIC SURGICAL DEVICE AND CONTROL ASSEMBLY FOR CUTTING A CORNEA

(76) Inventor: Johann F. Hellenkamp, 10060 SW. 89th Ct., Miami, FL (US) 33176

( * ) Notice: Subject to any disclaimer, the term of this patent is extended or adjusted under 35 U.S.C. 154(b) by 452 days.

This patent is subject to a terminal disclaimer.

(21) Appl. No.: 10/062,178

(22) Filed: Jan. 31, 2002

(65) Prior Publication Data

US 2003/0144678 A1    Jul. 31, 2003

Related U.S. Application Data

(63) Continuation-in-part of application No. 09/841,165, filed on Apr. 24, 2001, now abandoned, which is a continuation of application No. 08/840,430, filed on Apr. 29, 1997, now Pat. No. 6,296,649, which is a continuation of application No. 08/598,180, filed on Feb. 7, 1996, now Pat. No. 5,624,456, and a continuation-in-part of application No. 09/065,848, filed on Apr. 24, 1998, now Pat. No. 6,007,553, which is a continuation-in-part of application No. 08/845,171, filed on Apr. 25, 1997, now Pat. No. 6,051,009, and a continuation-in-part of application No. 09/690,204, filed on Oct. 17, 2000, now Pat. No. 6,605,099, which is a continuation of application No. 09/433,478, filed on Nov. 4, 1999, now Pat. No. 6,132,446, and a continuation-in-part of application No. 09/433,479, filed on Nov. 4, 1999, now Pat. No. 6,527,788.

(51) Int. Cl.
*A61B 17/32* (2006.01)

(52) U.S. Cl. ...................................... 606/166

(58) Field of Classification Search ................ 606/166, 606/167, 132
See application file for complete search history.

(56) References Cited

U.S. PATENT DOCUMENTS 679,779 A    8/1901    Pierpont (Continued)

FOREIGN PATENT DOCUMENTS

AU    1997 18543 B2    8/1997

(Continued)

OTHER PUBLICATIONS

Mueller, "The Surgical Armamentarium", (1980) pp. 2-5 and cover page.*

(Continued)

*Primary Examiner*—Michael Thaler
(74) *Attorney, Agent, or Firm*—Malloy & Malloy, P.A.

(57) ABSTRACT

A surgical device for cutting substantially across a cornea of an eye of a patient, the device including a positioning ring to be attached to an eye surrounding a cornea to be cut, and defining an aperture sized to receive and expose the cornea to be cut. The surgical device further includes a cutting head assembly structured to be guided and driven over an upper surface of the positioning ring in a generally arcuate path, and having a cutting element positioned therein and structured to oscillate laterally to facilitate smooth and effective cutting of the cornea. The cutting head assembly is structured to be detachably coupled to the positioning ring by a coupling member which permits movement of the cutting head assembly relative to the positioning ring along the generally arcuate path, but maintains sufficient engagement therebetween to ensure that smooth, steady, driven movement is maintained.

36 Claims, 9 Drawing Sheets

U.S. PATENT DOCUMENTS

| | | |
|---|---|---|
| 727,396 A | 5/1903 | Luhrman |
| 936,667 A | 10/1909 | Reynolds |
| 1,092,367 A | 4/1914 | Knapp |
| 1,400,379 A | 12/1921 | Schollmeyer |
| 1,440,325 A | 12/1922 | Wilhelm |
| 1,617,924 A | 2/1927 | Russell |
| 1,660,134 A | 2/1928 | Mernit |
| 1,761,260 A | 6/1930 | Gallasch |
| 1,896,828 A | 2/1933 | Nichterlein |
| 1,974,606 A | 9/1934 | Fassin |
| 2,015,160 A | 9/1935 | Shaler |
| 2,457,772 A | 12/1948 | Brown et al. |
| 2,486,645 A | 11/1949 | Hager |
| 2,539,597 A | 1/1951 | Staples |
| 2,648,138 A | 8/1953 | Gase |
| 2,697,433 A | 12/1954 | Zehnder |
| 2,912,843 A | 11/1959 | Williams |
| 3,025,598 A | 3/1962 | Nissen |
| 3,074,407 A | 1/1963 | Moon et al. |
| 3,111,872 A | 11/1963 | Trippler |
| 3,167,868 A | 2/1965 | Arneson |
| 3,217,416 A | 11/1965 | Bachert et al. |
| 3,231,982 A | 2/1966 | Ribich |
| 3,316,635 A | 5/1967 | Merrow et al. |
| 3,331,650 A | 7/1967 | Williams |
| 3,412,732 A | 11/1968 | Simon |
| 3,428,045 A | 2/1969 | Kratzsch et al. |
| 3,508,835 A | 4/1970 | Ware |
| 3,535,793 A | 10/1970 | Williams et al. |
| 3,554,197 A | 1/1971 | Dobbie |
| 3,577,637 A | 5/1971 | Braginetz |
| 3,583,403 A | 6/1971 | Pohl et al. |
| 3,606,550 A | 9/1971 | Proksa |
| 3,701,199 A | 10/1972 | Lewis |
| 3,708,881 A | 1/1973 | Bennett |
| 3,846,008 A | 11/1974 | Sobajima et al. |
| 3,879,847 A | 4/1975 | Roll |
| 3,905,374 A | 9/1975 | Winter |
| 4,173,980 A | 11/1979 | Curtin |
| 4,180,075 A | 12/1979 | Marinoff |
| 4,205,682 A | 6/1980 | Crock et al. |
| 4,207,790 A | 6/1980 | Endo |
| 4,211,232 A | 7/1980 | Mormann et al. |
| 4,265,023 A | 5/1981 | Frost et al. |
| 4,271,740 A | 6/1981 | Yamazaki et al. |
| 4,298,004 A | 11/1981 | Schachar et al. |
| 4,329,785 A | 5/1982 | Peterson |
| 4,393,587 A | 7/1983 | Kloosterman |
| 4,414,749 A | 11/1983 | Johannsmeier |
| 4,423,728 A | 1/1984 | Lieberman |
| 4,429,696 A | 2/1984 | Hanna |
| 4,438,567 A | 3/1984 | Raiha |
| 4,452,235 A | 6/1984 | Reynolds |
| 4,489,489 A | 12/1984 | Sarto |
| 4,490,885 A | 1/1985 | Iskiw et al. |
| 4,495,701 A | 1/1985 | Nakadoi |
| 4,499,898 A | 2/1985 | Knepshield et al. |
| 4,515,157 A | 5/1985 | Fedorov et al. |
| 4,517,741 A | 5/1985 | Castelluzzo |
| 4,526,171 A | 7/1985 | Schachar |
| 4,538,356 A | 9/1985 | Knepshield et al. |
| 4,546,773 A | 10/1985 | Kremer et al. |
| 4,565,198 A | 1/1986 | Koeniger |
| 4,598,714 A | 7/1986 | Kremer et al. |
| 4,607,617 A | 8/1986 | Choyce |
| 4,619,259 A | 10/1986 | Graybill et al. |
| 4,630,378 A | 12/1986 | Kulp et al. |
| 4,637,393 A | 1/1987 | Ray |
| 4,642,892 A | 2/1987 | Ishida |
| 4,648,400 A | 3/1987 | Schneider et al. |
| 4,660,556 A | 4/1987 | Swinger et al. |
| 4,662,075 A | 5/1987 | Mastel et al. |
| 4,662,370 A | 5/1987 | Hoffmann et al. |
| 4,662,881 A | 5/1987 | Nordan |
| 4,665,914 A | 5/1987 | Tanne |
| 4,671,276 A | 6/1987 | Reynolds |
| 4,672,964 A | 6/1987 | Dee et al. |
| 4,674,503 A | 6/1987 | Peyman et al. |
| 4,676,790 A | 6/1987 | Kern |
| 4,688,570 A | 8/1987 | Kramer et al. |
| 4,718,418 A | 1/1988 | L'Esperance, Jr. |
| 4,723,545 A | 2/1988 | Nixon et al. |
| 4,744,144 A | 5/1988 | Lowery, Sr. et al. |
| 4,750,489 A | 6/1988 | Berkman et al. |
| 4,750,491 A | 6/1988 | Kaufman et al. |
| 4,766,895 A | 8/1988 | Reynolds |
| 4,768,509 A | 9/1988 | Grosvenor et al. |
| 4,788,976 A | 12/1988 | Dee |
| 4,796,623 A | 1/1989 | Krasner et al. |
| 4,807,623 A | 2/1989 | Lieberman |
| 4,813,132 A | 3/1989 | Castelluzzo |
| 4,815,218 A | 3/1989 | Gordy |
| 4,815,463 A | 3/1989 | Hanna |
| 4,821,357 A | 4/1989 | Millette |
| 4,826,042 A | 5/1989 | Vujovich |
| 4,834,748 A | 5/1989 | McDonald |
| 4,835,865 A | 6/1989 | Knoop |
| 4,840,175 A | 6/1989 | Peyman |
| 4,844,070 A | 7/1989 | Dee |
| 4,865,033 A | 9/1989 | Krumeich et al. |
| 4,884,569 A | 12/1989 | Fedorov et al. |
| 4,884,570 A | 12/1989 | Krumeich et al. |
| 4,898,170 A | 2/1990 | Hofmann et al. |
| 4,900,300 A | 2/1990 | Lee |
| 4,903,695 A | 2/1990 | Warner et al. |
| 4,914,816 A | 4/1990 | Fenn et al. |
| 4,917,086 A | 4/1990 | Feltovich et al. |
| 4,943,296 A | 7/1990 | Funakubo et al. |
| 4,994,081 A | 2/1991 | Civerchia et al. |
| 4,997,437 A | 3/1991 | Grieshaber |
| 5,007,169 A | 4/1991 | Motta |
| 5,009,660 A | 4/1991 | Clapham |
| 5,011,498 A | 4/1991 | Krumeich et al. |
| 5,055,106 A | 10/1991 | Lundgren |
| 5,063,942 A | 11/1991 | Kilmer et al. |
| 5,084,059 A | 1/1992 | Metzger |
| 5,092,863 A | 3/1992 | Schanzlin |
| 5,105,545 A | 4/1992 | Fletcher |
| 5,108,412 A | 4/1992 | Krumeich et al. |
| 5,112,350 A | 5/1992 | Civerchia et al. |
| 5,133,726 A | 7/1992 | Ruiz et al. |
| 5,139,518 A | 8/1992 | White |
| 5,152,786 A | 10/1992 | Hanna |
| 5,171,254 A | 12/1992 | Sher |
| 5,178,626 A | 1/1993 | Pappas |
| 5,188,125 A | 2/1993 | Kilmer et al. |
| 5,201,747 A | 4/1993 | Mastel |
| 5,203,865 A | 4/1993 | Siepser |
| 5,215,104 A | 6/1993 | Steinert |
| 5,217,477 A | 6/1993 | Lager |
| 5,222,960 A | 6/1993 | Poley |
| 5,222,967 A | 6/1993 | Casebeer et al. |
| 5,222,967 A | 6/1993 | Casebeer et al. |
| 5,222,976 A | 6/1993 | Yoon |
| 5,224,950 A | 7/1993 | Prywes |
| 5,226,905 A | 7/1993 | Hanna |
| 5,232,568 A | 8/1993 | Parent et al. |
| 5,269,795 A | 12/1993 | Arnott |
| 5,288,292 A | 2/1994 | Giraud et al. |
| 5,290,301 A | 3/1994 | Lieberman |
| 5,299,354 A | 4/1994 | Metcalf et al. |
| 5,306,282 A | 4/1994 | Muller |
| 5,308,355 A | 5/1994 | Dybbs |
| 5,312,394 A | 5/1994 | Beckman |

| | | | | | | |
|---|---|---|---|---|---|---|
| 5,318,044 | A | 6/1994 | Kilmer et al. | 5,857,995 A | 1/1999 | Thomas et al. |
| 5,318,046 | A | 6/1994 | Rozakis | 5,868,771 A * | 2/1999 | Herbert et al. .............. 606/167 |
| 5,336,235 | A | 8/1994 | Myers | 5,871,492 A | 2/1999 | Sorensen |
| 5,336,236 | A | 8/1994 | Nevyas-Wallace | 5,873,881 A | 2/1999 | McEwen et al. |
| 5,337,482 | A | 8/1994 | Schmidt | 5,876,415 A | 3/1999 | Pierce et al. |
| 5,342,377 | A | 8/1994 | Lazerson | 5,876,439 A | 3/1999 | Lee |
| 5,342,378 | A | 8/1994 | Giraud et al. | 5,934,285 A | 8/1999 | Kritzinger et al. |
| 5,352,233 | A | 10/1994 | Anis | 5,935,140 A | 8/1999 | Buratto |
| 5,368,604 | A | 11/1994 | Kilmer et al. | 5,944,731 A | 8/1999 | Hanna |
| 5,370,652 | A | 12/1994 | Kellan | 5,947,987 A | 9/1999 | Gordon et al. |
| 5,376,099 | A | 12/1994 | Ellis et al. | 5,964,748 A | 10/1999 | Peyman |
| 5,395,385 | A | 3/1995 | Kilmer et al. | 5,964,775 A | 10/1999 | Gordon et al. |
| 5,403,335 | A | 4/1995 | Loomas et al. | 5,964,776 A | 10/1999 | Peyman |
| 5,405,355 | A | 4/1995 | Peyman et al. | 5,976,163 A | 11/1999 | Nigam |
| 5,411,510 | A | 5/1995 | Fugo | 5,980,543 A | 11/1999 | Carriazo et al. |
| 5,411,511 | A | 5/1995 | Hall | 5,989,272 A | 11/1999 | Barron et al. |
| 5,423,840 | A | 6/1995 | Casebeer et al. | 5,997,559 A | 12/1999 | Ziemer |
| 5,423,841 | A | 6/1995 | Kornefeld | 6,007,553 A | 12/1999 | Hellenkamp et al. |
| 5,431,671 | A | 7/1995 | Nallakrishnan | 6,022,364 A | 2/2000 | Flumene et al. |
| 5,437,657 | A | 8/1995 | Epstein | 6,022,365 A | 2/2000 | Aufaure et al. |
| 5,441,511 | A | 8/1995 | Hanna | 6,030,398 A | 2/2000 | Klopotek |
| 5,441,512 | A | 8/1995 | Muller | 6,033,075 A | 3/2000 | Fujieda et al. |
| 5,447,517 | A | 9/1995 | Steen et al. | 6,033,418 A | 3/2000 | Gordon et al. |
| 5,458,610 | A | 10/1995 | Feaster | 6,036,709 A | 3/2000 | Boutros |
| 5,464,417 | A | 11/1995 | Eick | 6,042,594 A | 3/2000 | Hellenkamp |
| 5,486,188 | A | 1/1996 | Smith | 6,045,562 A | 4/2000 | Amano et al. |
| 5,489,299 | A | 2/1996 | Schachar | 6,051,009 A | 4/2000 | Hellenkamp et al. |
| 5,496,339 | A | 3/1996 | Koepnick | 6,056,764 A | 5/2000 | Smith |
| 5,507,741 | A | 4/1996 | L'Esperance, Jr. | 6,059,805 A | 5/2000 | Sugimura et al. |
| 5,507,759 | A | 4/1996 | Nordan | 6,071,293 A | 6/2000 | Krumeich |
| 5,527,328 | A | 6/1996 | Pintucci | 6,080,166 A | 6/2000 | McEwen et al. |
| 5,529,581 | A | 6/1996 | Cusack | 6,083,236 A | 7/2000 | Feingold |
| 5,545,172 | A | 8/1996 | Knepshield et al. | 6,090,119 A | 7/2000 | Pierce et al. |
| 5,549,139 | A | 8/1996 | Perkins et al. | 6,099,541 A | 8/2000 | Klopotek |
| 5,549,622 | A | 8/1996 | Ingram | 6,117,149 A | 9/2000 | Sorensen et al. |
| 5,556,406 | A | 9/1996 | Gordon et al. | 6,126,668 A | 10/2000 | Bair et al. |
| 5,562,691 | A | 10/1996 | Tano et al. | 6,132,446 A | 10/2000 | Hellenkamp et al. |
| 5,562,693 | A | 10/1996 | Devlin et al. | 6,136,012 A | 10/2000 | Chayet et al. |
| 5,571,124 | A | 11/1996 | Zelman | 6,139,559 A | 10/2000 | Nordan et al. |
| 5,586,980 | A | 12/1996 | Kremer et al. | 6,139,560 A | 10/2000 | Kremer |
| RE35,421 | E | 1/1997 | Ruiz et al. | 6,143,011 A | 11/2000 | Hood et al. |
| 5,591,174 | A | 1/1997 | Clark et al. | 6,149,609 A | 11/2000 | Lieberman et al. |
| 5,591,185 | A | 1/1997 | Kilmer et al. | 6,149,661 A | 11/2000 | Graczyk |
| 5,595,570 | A | 1/1997 | Smith | 6,165,189 A | 12/2000 | Ziemer |
| 5,603,365 | A | 2/1997 | Stewart | 6,176,853 B1 | 1/2001 | Stolyarenko |
| 5,619,889 | A | 4/1997 | Jones et al. | 6,183,488 B1 | 2/2001 | Ross et al. |
| 5,620,453 | A | 4/1997 | Nallakrishnan | 6,185,823 B1 | 2/2001 | Brown et al. |
| 5,624,456 | A | 4/1997 | Hellenkamp | 6,197,038 B1 | 3/2001 | O'Donnell, Jr. |
| 5,632,757 | A | 5/1997 | Arnott | 6,203,555 B1 | 3/2001 | Amano et al. |
| 5,634,918 | A | 6/1997 | Richards | 6,228,099 B1 | 5/2001 | Dybbs |
| 5,643,299 | A | 7/1997 | Bair | 6,231,583 B1 | 5/2001 | Lee |
| 5,658,303 | A | 8/1997 | Koepnick | 6,254,619 B1 | 7/2001 | Garabet et al. |
| 5,662,668 | A | 9/1997 | Kurwa | 6,258,110 B1 | 7/2001 | Hellenkamp |
| 5,662,669 | A * | 9/1997 | Abidin et al. .............. 606/167 | 6,296,649 B1 | 10/2001 | Hellenkamp |
| 5,669,144 | A | 9/1997 | Hahn et al. | 6,387,107 B1 | 5/2002 | Hellenkamp |
| 5,674,233 | A | 10/1997 | Dybbs | 6,527,788 B1 | 3/2003 | Hellenkamp |
| 5,683,592 | A | 11/1997 | Bartholomew et al. | 2002/0082628 A1 | 6/2002 | Hellenkamp |
| 5,690,123 | A | 11/1997 | Medina | 2002/0091401 A1 | 7/2002 | Hellenkamp |
| 5,690,641 | A | 11/1997 | Sorensen et al. | | | |
| 5,690,657 | A | 11/1997 | Koepnick | | FOREIGN PATENT DOCUMENTS | |
| 5,695,509 | A | 12/1997 | El Hage | | | |
| 5,700,274 | A | 12/1997 | Feaster | AU | 706115 | 6/1999 |
| 5,713,915 | A | 2/1998 | Van Heugten et al. | BR | PI9707374-1 | 4/1999 |
| 5,733,334 | A | 3/1998 | Lee | CN | 1089824 | 7/1994 |
| 5,772,675 | A | 6/1998 | Hellenkamp | DE | 28 180 73 A1 | 10/1978 |
| 5,779,723 | A | 7/1998 | Schwind | DE | 31 476 62 A1 | 6/1983 |
| 5,792,161 | A | 8/1998 | de Almeida Cunha | DE | 34 335 81 A1 | 3/1986 |
| 5,807,380 | A | 9/1998 | Dishler | DE | 38 255 87 A1 | 2/1990 |
| 5,807,381 | A | 9/1998 | Lieberman | DE | 40 128 82 A1 | 10/1991 |
| 5,810,857 | A | 9/1998 | Mackool | EP | 0 261 242 A1 | 3/1988 |
| 5,817,115 | A | 10/1998 | Nigam | EP | 0 442 156 A1 | 8/1991 |
| 5,833,701 | A | 11/1998 | Gordon | EP | 0 442 156 B1 | 8/1991 |
| 5,855,604 | A | 1/1999 | Lee | EP | 0 531 756 A2 | 3/1993 |

| | | |
|---|---|---|
| EP | 0 555 625 A1 | 8/1993 |
| EP | 0 873 735 A1 | 10/1998 |
| EP | 0 900 554 A1 | 3/1999 |
| EP | 0 977 532 B1 | 9/2003 |
| FR | 1.366.323 | 7/1964 |
| FR | 2 660 547 | 10/1991 |
| FR | 2 693 368 | 1/1994 |
| FR | 2 751 206 | 1/1998 |
| FR | 20000013067 | 10/2000 |
| FR | 20010005228 | 4/2001 |
| GB | 2 092 008 A | 8/1982 |
| GB | 2 095 119 A | 9/1982 |
| GB | 2 113 550 A | 8/1983 |
| GB | 2 129 957 A | 5/1984 |
| GB | 2 178 324 A | 2/1987 |
| GB | 2 179 859 A | 3/1987 |
| GB | 2 242 835 A | 10/1991 |
| GB | 2 247 174 A | 2/1992 |
| JP | 48-23098 | 3/1973 |
| JP | 59-22545 | 2/1984 |
| JP | 61-73657 | 4/1986 |
| JP | 5-72827 | 10/1993 |
| SG | 68725 | 10/1867 |
| SG | 200000056167 | 9/2000 |
| SU | 1463253 A1 | 3/1989 |
| SU | 1657180 A1 | 6/1991 |
| SU | 1685417 A1 | 10/1991 |
| WO | WO 82/00759 | 3/1982 |
| WO | WO 87/05799 | 10/1987 |
| WO | WO 93/06783 | 4/1993 |
| WO | WO 93/09738 | 5/1993 |
| WO | WO 94/01067 | 1/1994 |
| WO | WO 95/31143 | 11/1995 |
| WO | WO 96/13216 | 5/1996 |
| WO | WO 98/27901 | 7/1998 |
| WO | WO 99/26568 | 6/1999 |
| WO | WO 00/56222 | 9/2000 |

OTHER PUBLICATIONS

Summons & Complaint, BLMM01.
Answer of Moria, S.A., BLMM02.
Answer of Microtech, Inc., BLMM03.
Moria's First Interrogatories, BLMM04.
Defendants' First Request for Production of Documents, BLMM05.
B&L's Combined Motion to Dismiss/Motion to Strike [and proposed Order], BLMM06.
Defendants' Brief in Opposition to Plaintiff's Motion to Dismiss or Strike Their Counterclaim, BLMM07.
Order, BLMM08.
Amended Answer to Moria, S.A., BLMM09.
Amended Answer to Microtech, Inc., BLMM10.
B&L's Answer to the Amended Counterclaim of Moria, BLMM11.
B&L's Answer to the Amended Counterclaim of Microtech, BLMM12.
B&L's Interrogatories to Defendant Moria, BLMM13.
B&L's Interrogatories to Defendant Microtech, BLMM14.
B&L's First Set of Request for Production and Things to Defendants Moria and Microtech, BLMM15.
(Proposed) First Amended Complaint, BLMM16.
B&L's Interrogatories to Defendant Moria, BLMM17.
B&L's Interrogatories to Defendant Microtech, BLMM18.
B&L's First Set of Request for Production of Documents and Things to Defendants Moria and Microtech, BLMM19.
First Amended Complaint, BLMM20.
B&L's Second Interrogatories (No. 5) to Defendant Microtech, BLMM21.
B&L's Second Set of Request for Production (Nos. 61-81) of Documents and Things to Defendants, BLMM22.
B&L's Second Interrogatories (No. 5) to Defendant Moria, BLMM23.
Stipulation, BLMM24.
Answer of Moria S.A. to First Amended Complaint, BLMM25.
Answer of Microtech, Inc. to First Amended Complaint, BLMM26.
B&L's Amended Answer to Moria's Counterclaim, BLMM27.
B&L's Amended Answer to Microtech's Counterclaim, BLMM28.
B&L's Confidential Answers to Moria's First Interrogatories, BLMM29.
B&L's Answers to Moria's First Interrogatories, BLMM30.
B&L's Responses to Defendants' First Request for Production of Documents, BLMM31.
Moria, S.A. & Microtech, Inc.'s Response to B&L's First and Second Sets of Requests for Production, BLMM32.
Defendants' Response to B&L's First and Second Sets of Interrogatories, BLMM33.
Letter of Transmittal—B&L's Claim Charts, BLMM34.
Letter of Transmittal—Defendant's Response to Claim Charts, BLMM35.
Defendants' Second Request for Production of Documents, BLMM36.
Defendants' Second Set of Interrogatories, BLMM37.
B&L's Responses to Defendants' Second Request for Production of Documents, BLMM38.
B&L's Answers to Defendants' Second Set of Interrogatories, BLMM39.
Report of Roger F. Steinert, M.D., BLMM40.
Markman Report of J.E. Akin, Ph.D., P.E., BLMM41.
Second Amended Complaint [and Stipulation], BLMM42.
Rebuttal Report of Roger F. Steinert, M.D., BLMM43.
Rebuttal Report of Stephen G. Slade, M.D., BLMM44.
Answer of Moria S.A. and Microtech, Inc. to Second Amended Complaint, BLMM45.
Defendants' Markman Brief, BLMM46.
Plaintiff B&L's Brief in Support of Claim Construction [and (proposed) Order], BLMM47.
Plaintiff B&L's Second Amended Answer to Defendants' Counterclaim, BLMM48.
Defendants' Markman Reply Brief, BLMM49.
Plaintiff B&L's Reply to Defendants' Markman Brief, BLMM50.
Joint Exhibits for Markman Hearing, vol. 1 of 3, BLMM51.
Joint Exhibits for Markman Hearing, vol. 2 of 3, BLMM52.
Joint Exhibits for Markman Hearing, vol. 3 of 3, BLMM53.
Conclusions of Law Regarding Patent Claim Construction, BLMM54.
Plaintiff B&L's Request for Reconsideration of the Court's Apr. 16, 2002 Claim Construction, BLMM55.
Defendants' Brief in Opposition to Plaintiff's Request for Reconsideration of Markman Order, BLMM56.
Plaintiff B&L's Reply in Support of B&L's Request for Reconsideration of the Court's Apr. 16, 2002 Claim Construction, BLMM57.
Memorandum Sur Motion for Reconsideration of Patent Claim Construction, BLMM58.
Notice of Interested Parties Pursuant to Rule 4.6; Summons; Complaint for Patent, BLOM001.
Defendant Oasis Medical, Inc.'s Notice of Motion and Motion for Sanctions, Including Determine Sanctions Pursuant to Fed. R. Civ. Pro. Rule 11; Memorandum of Points and Authorities in Support Thereof; Declaration of Surjit P. Soni; and Exhibits A-I, BLOM002.
Defendant's Statement of Uncontroverted Material Facts and Conclusions of Law in Support of Motion for Summary Judgment, BLOM003.
Defendant's Notice of Motion and Motion for Summary Judgment; Memorandum of Points and Authorities in Support Thereof; Declaration of Surjit P. Soni; and Exhibits, BLOM004.
Defendant's Notice of Withdrawal of Motion for Summary Judgment, BLOM005.
Stipulation Continuing Time to Respond to the Complaint to Dec. 15th, 2000; and Order Thereon, BLOM006.
Bausch & Lomb Surgical, Inc.'s Interrogatories to Defendant, BLOM007.
B&L's Requests for Production of Documents and Things to Defendant, BLOM008.
B&L's Request for Admissions to Defendant, BLOM009.
Defendant's Notice of Motion and Motion for Summary Judgment; Memorandum of Points and Authorities in Support Thereof; Declaration of Surjit P. Soni; and Exhibits, BLOM010.

Defendant's Statement of Uncontroverted Material Facts and Conclusions of Law in Support of Motion for Summary Judgment, BLOM011.
B&L's Statement of Genuine Issues in Response to the Statement of Uncontroverted Facts and Conclusions of Law in Opposition to Defendant's Motion for Summary Judgment of Non-Infringement, BLOM012.
B&L's Written Evidentiary Objections to the Declaration of Surjit P. Soni and Exhibits Attached Thereto in Opposition to Defendant's Motion for Summary Judgment of Non-Infringement, BLOM013.
B&L's Memorandum of Points and Authorities in Opposition to Defendant's Motion for Summary Judgment of Non-Infringement, BLOM014.
B&L's Memorandum of Points and Authorities in Opposition to Defendant's Motion for Sanctions, BLOM015.
Declaration of Lester L. Hewitt and Accompanying Exhibits in Support of B&L's Opposition to Defendant's Motion for Sanctions, BLOM016.
Declarations of Stephen J. Hilmes, John J. Weidenbenner, John E. Akin and Gregory M. Hasley in Opposition to Defendant's Motion for Summary Judgment of Non-Infringement, BLOM017.
Declaration Exhibits in Support of B&L's Opposition to Defendant's Motion for Summary Judgment of Non-Infringement, BLOM018.
Defendant's Objections to the Declarations of Stephen J. Hilmes, John J. Weidenbenner, John E. Akin, Gregory M. Hasley and Lester L. Hewitt Filed in Opposition to Defendant's Motion for Summary Judgment, BLOM019.
Defendant's Reply in Support of Its Motion for Summary Judgment, BLOM020.
Defendant's Reply Brief in Support of Motion for Sanctions, Including to Determine Sanctions Pursuant to Fed. R. Civ. Pro. Rule 11, BLOM021.
Defendant's Objections to the Declaration of Lester L. Hewitt Filed in Opposition to Defendant's Motion for Sanctions, BLOM022.
Defendant's Reply to B&L's Written Evidentiary Objections to the Declaration of Surjit P. Soni and the Exhibits Attached Thereto, BLOM023.
Defendant's Answer and Affirmative Defenses to Complaint of B&L, and Counterclaims, BLOM024.
Notice of Interested Parties, BLOM025.
Defendant's Responses to B&L's Interrogatories; Set No.: One, BLOM026.
Defendant's Responses to B&L's Requests for Production of Documents and Things, BLOM027.
Defendant's Responses to B&L's Requests for Admissions, BLOM028.
Defendant's Notice of Motion and Second Motion for Summary Judgment; Memorandum of Points and Authorities in Support Thereof; Declaration of Surjit P. Soni and Norman Delgado; and Exhibits, BLOM029.
Defendant's Statement of Uncontroverted Material Facts and Conclusions of Law in Support of Motion for Summary Judgment, BLOM030.
B&L's Reply to Crossclaims of Defendant and Counter-Claimant Oasis Medical, Inc., BLOM031.
B&L's Initial Disclosures Under Local Rule 6.2 and F.R.C.P. 26 (a) (1), BLOM032.
Defendant's Rule 6 Disclosures, BLOM033.
Stipulation and [Proposed] Order Resetting Hearing Date on Defendant and Counter-Claimant's "Second" Motion for Summary Judgement, BLOM034.
Order Resetting Hearing Date on Defendant and Counter-Claimant's "Second" Motion for Summary Judgment, BLOM035.
Verification for Defendant's Responses to B&L's Interrogatories, Set No.: One, BLOM036.
B&L's Memorandum of Points and Authorities in Opposition to Defendant's Second Motion for Summary Judgment of Non-Infringement, BLOM037.
B&L's Statement of Genuine Issues of Material Fact in Opposition to Defendant's Second Motion for Summary Judgment, BLOM038.
Written Evidentiary Objections to the Declaration of Surjit P. Soni and Norman Delgado, and Exhibits Attached Thereto In Support B&L's Opposition to Defendant's Second Motion for Summary Judgment of Non-Infringement, BLOM039.
Declaration in Support of B&L's Opposition to Defendant's Second Motion for Summary Judgment of Non-Infringement, BLOM040.
Declaration Exhibits in Support of B&L's Opposition to Defendant's Second Motion for Summary Judgment of Non-Infringement, BLOM041.
Defendant's Reply in Support of Its Second Motion for Summary Judgment, BLOM042.
Defendant's Reply to B&L's Statement of Genuine Issues of Material Fact in Opposition to Defendant's Second Motion for Summary Judgment, BLOM043.
Defendant's Reply to B&L's Written Evidentiary Objections to the Declaration of Surjit P. Soni and Norman Delgado, BLOM044.
Defendant's Objection to the Declaration of Stephen J. Hilmes, John J. Weidenbenner, John E. Akin and Gregory M. Hasley Filed in Opposition to Defendant's Second Motion for Summary Judgment, BLOM045.
Defendant's First Set of Interrogatories to B&L, BLOM046.
Defendant's First Set of Requests for Admissions to B&L, BLOM047.
B&L's Reply to Defendant's Objections to Declarations of Hilmes, Weidenbenner, Akin, and Hasley Filed in Opposition to Defendant's Second Motion for Summary Judgment, BLOM048.
B&L's Request to File Sur-Reply to Defendant's Reply in Support of Its Second Motion for Summary Judgment, BLOM049.
B&L's Sur-Reply to Defendant's Reply in Support of Its Second Motion for Summary Judgment, BLOM050.
Order Granting B&L Leave to File Sur-Reply to Defendant's Reply in Support of Its Second Motion for Summary Judgment, BLOM051.
Scheduling and Case Management Order, BLOM052.
Defendant's First Set of Requests for Production of Documents to B&L, BLOM053.
Joint Submission re: Construction of Claim 54 in Connection with Defendant's Motion for Summary Judgment Filed Pursuant to Court Order of Feb. 12$^{th}$, 2001, BLOM054.
B&L's Response to Requests fo Admissions 1-28, BLOM055.
B&L's Answers and Objections to Interrogatories 1-19, BLOM056.
B&L's Responses to First Set of Requests for Production of Documents, BLOM057.
Joint Stipulation Requesting Status Conference and Order Thereon, BLOM058.
Protective Order, BLOM059.
B&L's First Supplemental Answers to Interrogatories 7 and 16, BLOM060.
Verification for B&L's Confidential First Supplemental Answer to Interrogatory 1; Verification for B&L's Confidential First Supplemental Answers to Interrogatories 7 and 16, BLOM061.
Supplemental Information Lodged in Response to Court Request, BLOM062.
Memorandum of Decision and Preliminary Claim Construction, BLOM063.
Memorandum of Decision, BLOM064.
Joint Submission Relating to Proposed Pre-trial Order for Claim Construction Hearing, BLOM065.
B&L's Amended Responses to Requests for Admissions 3-10, 15, 18, and 20, BLOM066.
B&L's Amended Responses to First Set of Requests for Production of Documents, Request Nos. 5, 6, 16-19, 28-123, 136-138, 149, 151, 153, 156, 161-165, 168-171, 178, 180-182, and 189-193, BLOM067.
B&L's First Amended Answers to Interrogatories 2 and 17 and Second Amended Answers to Interrogatories 9-15, BLOM068.
Defendant's Supplemental Responses to B&L's Requests for Production of Documents and Things, BLOM069.
Revised Notice of Defendant's Motion to Compel Further Responses to Discovery, BLOM070.
Stipulation and [Proposed] Order re: Hearing Time on Defendant's Motion to Compel Further Discovery Responses or, in the Alternative, Permission to Appear Telephonically, BLOM071.
Supplemental Joint Submission Relating to Proposed Pre-Trial Order for Claim Construction Hearing, BLOM072.

B&L's Supplemental Memorandum Opposing Defendant's Motion to Compel, BLOM073.
Defendant's Supplemental Memorandum Regarding Defendant's Motion to Compel Further Responses to Discovery, BLOM074.
Joint Submission Relating to Proposed Pre-Trial Order for Claim Construction Hearing Pursuant to Court Order of Oct. 22, 2001, BLOM075.
Stipulation and Order re: Hearing Time on Defendant's Motion to Compel Further Discovery Responses or, in the Alternative, Permission to Appear Telephonically, BLOM076.
Civil Minutes—General (including Order re: Defendant's Motion to Compel Further Response to Discover), BLOM077.
B&L's Second Amended Answer to Interrogatory 2 and Third Amended Answer to Interrogatory 12, BLOM078.
Notice of Ex Parte Application and Ex Parte Application of Defendant Requesting Scheduling of Markman Hearing; Declaration of Daniel Harrison Wu, BLOM079.
Opposition in Part by B&L to Defendant's Ex Parte Application re: Markman Hearing, BLOM080.
Defendant's Reply to B&L's Opposition Regarding Scheduling of Markman Hearing; Declaration of Surjit P. Soni, BLOM081.
Ex Parte Application to Continue Status Conference Date by B&L; Memorandum of Points and Authorities; Declarations of Jay C. Gandhi and David R. Clonts in Support Thereof, BLOM082.
Defendant's Reply to B&L's Opposition Regarding Scheduling of Markman Hearing; Declaration of Surjit P. Soni, BLOM083.
Defendant's Opposition to Ex Parte Application to Continue Status Conference Date by B&L; Declaration of Daniel Harrison Wu, BLOM084.
Declaration Of David R. Clonts, BLOM085.
Supplement/Revision to Joint Submission of Oct. 25, 2001 Relating to Proposed Pre-trial Order for Claim Construction Hearing, BLOM086.
Stipulation for Claim Construction Hearing; [Proposed] Order, BLOM087.
Stipulation for Claim Construction Hearing; Order, BLOM088.
B&L's Initial Claim Construction Position re: U.S. Patent No. 6,051,009, BLOM089.
B&L's Second Set of Requests for Production Nos. 84-128 to Defendant, BLOM090.
Defendant's Initial Claim Construction Position re: U.S. Patent No. 6,051,009, BLOM091.
Defendant's Second Supplemental Responses to B&L's Interrogatories [Redacted], BLOM092.
Defendant's Responses to B&L's Requests for Production of Documents (Set No. Two), BLOM093.
Expert Report of Douglas J. Mastel Regarding Claim Interpretation, BLOM094.
Expert Report of Dr. James Salz Regarding Claim Interpretation, BLOM095.
Stipulation That Parties Will Not Present Patent Law Experts at Markman Hearing: Order, BLOM096.
Stipulation for Increase of the Maximum Number of Interrogatories; Order, BLOM097.
Stipulation to File First Amended Complaint; Order, BLOM098.
First Amended Complaint for Patent Infringement, BLOM099.
Notice of Depostion of Johann F. Hellenkamp, BLOM100.
Notice of Deposition of Richard J. Sherin, BLOM101.
Amended Notice of Deposition of Johann F. Hellenkamp; Subpoena, BLOM102.
Amended Notice of Deposition of Richard J. Sherin; Subpoena, BLOM103.
Rebuttal to the Expert Reports of Douglas J. Mastel and Dr. James Salz, BLOM104.
Defendant's Answer To First Amended Complaint And Counterclaims, BLOM105.
Notice Of Interested Parties, BLOM106.
Rebuttal Report of Stephen G. Slade, M.D., BLOM107.
Amended Notice of Depostition of Johann F. Hellenkamp, BLOM108.
Amended Notice of Deposition of Richard J. Sherin, BLOM109.
Stipulation Regarding Discovery; Order, BLOM110.
Notice of Deposition of Dr. James J. Salz, BLOM 111.
Notice of Deposition of Douglas J. Mastel, BLOM112.
B&L's Supplemental Claim Construction Position re: U.S. Patent No. 6,051,009, BLOM113.
Notice of Depostion Of John E. Akin; Subpoena, BLOM114.
Notice of Depostition Of Stephen G. Slade; Subpoena, BLOM115.
Stipulation Amending Protective Order, BLOM116.
Response and Objections of Non-Party Stephen G. Slade to Defendant's Subpoena for Production of Documents, BLOM117.
Response and Objections of Non-Party John E. Akin to Defendant's Subpoena for Production of Documents, BLOM118.
Amended Notice of Deposition Of John E. Akin, BLOM119.
Amended Notice of Depostition Of Stephen G. Slade, BLOM120.
Objections of Non-Party Douglas J. Mastel and Defendant to B&L's Subpoena for Production of Documents, BLOM121.
Defendant's Third Supplemental Responses to B&L's Interrogatories, BLOM122.
Stipulation to One Day Extension of Cutoff for Markman Depositions, BLOM123.
B&L's Memorandum of Points and Authorities in Support of Claim Construction, BLOM124.
Exhibits to B&L's Memorandum of Points and Authorities in Support of Claim Construction, BLOM125.
Proposed Order Granting B&L's Claim Construction, BLOM126.
Stipulation to the Construction of Certain "Means for Engaging" and "Means for Being Operably Driven" Terms, BLOM127.
Notice of Filing Under Seal Defendant's Opening Markman Brief and Second Declaration of Ben M. Davidson in Support of Defendant's Proposed Claim Construction, BLOM128.
First Declaration of Ben M. Davidson in Support of Defendant's Proposed Claim Construction, BLOM129.
Declaration of James Salz, M.D. in Support of Defendant's Proposed Claim Construction, BLOM130.
Declaration of Douglas J. Mastel in Support of Defendant's Proposed Claim Construction, BLOM131.
Stipulation to One Week Extension for Rebuttal Expert Report of Dr. Stephen G. Slade; Order, BLOM132.
Supplemental Listing of Cases in Which Dr. Salz has Testified as an Expert in Last Four Years, BLOM133.
Notice of Application and Application for Order Authorizing Filing Under Seal; [Proposed] Order Authorizing Filing Under Seal, BLOM134.
Exhibits to B&L's Memorandum of Points and Authorities In Support of Its Motion to Exclude Expert Testimony, BLOM135.
Proposed Order Granting B&L's Motion to Exclude Expert Testimony, BLOM136.
Stipulation and [Proposed] Order re: Markman Hearing, BLOM137.
Civil Minutes—General (including Order Authorizing Filing Under Seal: B&L's Notice of Motion and Motion to Exclude Expert Testimony; Memorandum of Points and Authorities; Exhibit No. 5 of B&L's Motion to Exclude Expert Testimony), BLOM138.
Notice of Filing Under Seal Defendant's Memorandum of Points and Authorities, Statement of Uncontroverted Facts and Conclusions of Law, and Declaration of Andrew Eliseev in Support of Defendant's Motion for Summary Judgment of Invalidity of the Asserted Claims of the '009 Patent for Failure to Comply with the Best Mode Requirement of 35 U.S.C. § 112, Paragraph One, BLOM139.
Notice of Motion and Motion of Defendant for Summary Judgment of Invalidity of the Asserted Claims of the '009 Patent for Failure to Comply with the Best Mode Requirement of 35 U.S.C. § 112, Paragraph One; [Proposed] Order Granting Defendant's Motion for Summary Judgment of Invalidity of the Asserted Claims of the '009 Patent for Failure to Comply with the Best Mode Requirement of 35 U.S.C. § 112, Paragraph One, BLOM140.
Defendant's Response to B&L's Opening Markman Brief, BLOM141.
Third Declaration of Ben M. Davidson in Support of Defendant's Response to B&L's Opening Markman Brief, BLOM142.
Declaration of Ben M. Davidson Supporting Defendant's Opposition to B&L's Motion to Exclude Expert Testimony, BLOM143.
B&L's Opposition to Defendant's Opening Markman Brief, BLOM144.

Declaration of David R. Clonts with Attached Exhibits in Support of B&L's Opposition to Defendant's Opening Markman Brief, BLOM145.
Stipulation and [Proposed] Order re: Extensions for Briefing on Defendant's Motion for Summary Judgment, BLOM146.
Errata re: Color pp. 22 and 23 in B&L's Opposition to Defendant's Opening Markman Brief, BLOM147.
[PROPOSED] Order Granting Errata re: Color pp. 22 and 23 in B&L's Opposition to Defendant's Opening Markman Brief, BLOM148.
B&L's Reply to Defendant's Opposition to Motion to Strike Experts, BLOM149.
Declaration of David R. Clonts with Attached Exhibits In Support of B&L's Reply to Defendant's Opposition to Motion to Strike Experts, BLOM150.
Order Granting Errata re: Color pp. 22 and 23 in B&L's Opposition to Defendant's Opening Markman Brief, BLOM151.
Notice of Application and Application for Order Authorizing Filing Under Seal, BLOM152.
Notice of Filing Under Seal B&L's Memorandum of Points and Authorities, Declaration of Gregory M. Hasley with Attached Exhibits, and Statement of Genuine Issues of Material Fact in Opposition to Defendant's Motion for Summary Judgment on Best Mode, BLOM153.
Declaration of Gregory M. Hasley with Attached Exhibits in Support of B&L's Opposition to Defendant's Motion for Summary Judgment on the Best Mode Issue [Redacted], BLOM154.
[Proposed] Order Authorizing Filing Under Seal, BLOM155.
Defendant's Reply to B&L's Opposition Markman Brief, BLOM156.
Fourth Declaration of Ben M. Davidson in Support of Defendant's Reply to B&L's Opposition Markman Brief, BLOM157.
B&L's Reply to Defendant's Response to B&L's Opening Markman Brief, BLOM158.
Declaration of David R. Clonts with Attached Exhibits in Support of B&L's Reply to Defendant's Response to B&L's Opening Markman Brief, BLOM159.
Stipulation to the Construction of Certain "Means for Engaging" and "Means for Being Operably Driven" Terms, BLOM160.
Order Authorizing Filing Under Seal, BLOM161.
B&L's Markman Hearing Exhibit List, BLOM162.
Defendant's Demonstratives and Trial Director Slides for the Markman Hearing, BLOM163.
B&L's Demonstratives for the Markman Hearing, BLOM164.
Independent Claims of the '009 Patent at Issue, BLOM165.
Amended B&L's Markman Hearing Exhibit List, BLOM166.
Joint Proposed Agenda re: Markman Hearing, BLOM167.
Defendant's Markman Exhibit List, BLOM168.
Notice of Lodging of Deposition Transcripts of Johann Hellenkamp, James J. Salz, Douglas J. Mastel, John Edward Akin, Stephen G. Slade, BLOM169.
Amended B&L Markman Hearing Exhibit List, BLOM170.
Defendant's Markman Hearing Exhibits, BLOM171.
Memorandum of Decision re: Claim Construction, BLOM172.
Memorandum of Decision re: Defendant's Motion for Summary Judgment of Invalidity of the Asserted Claims of the '009 Patent for Failure to Comply with the Best Mode Requirement of 35 U.S.C. § 112, Paragraph One, BLOM173.
Stipulation for Case Management Schedule; [Proposed] Order, BLOM174.
Stipulation for Case Management Schedule; Order, BLOM175.
Notice of Videotaped Deposition of Robert Austring, BLOM176.
Notice of Videotaped Deposition of Michael J. Ram, BLOM177.
Notice of Videotaped Deposition of William Hagel, BLOM178.
Subpeona for Documents to Michael J. Ram, BLOM179.
Defendant's Fourth Supplemental Responses to B&L's Interrogatories, BLOM180.
B&L's Cumulative Amended Answers and Objections to Interrogatories 1-19, BLOM181.
B&L's Second Amended Responses to First Set of Requests for Production of Documents, BLOM182.
Objections of Non-Party Michael J. Ram and Defendant to B&L's Subpoena for Production of Documents, BLOM183.

Notice of Taking Videotaped Deposition of Eric Weinberg and Request for Production of Documents; Subpoena, BLOM184.
Stipulation to File First Amended Answer to First Amended Complaint and Counterclaims; [Proposed] Order; Defendant's First Amended Answer to First Amended Complaint and Counterclaims, BLOM185.
Notice of Taking Videotaped Deposition of Eric Weinberg and Request for Production of Documents; Subpeona, BLOM186.
Defendant's Second Set of Requests for Documents and Things to B&L (Nos. 197-200), BLOM187.
Defendant's Fifth Supplemental Responses to B&L's Interrogatories (No. 8), BLOM188.
Notice of Taking Videotaped Depostition of Johann F. Hellenkamp and Request for Production of Documents; Subpoena, BLOM189.
Notice of Subpoena Duces Tecum to Micra USA, Inc.; Subpoena, BLOM190.
Notice of Subpoena Duces Tecum to Moria S.A.; Subpoena, BLOM191.
Notice of Videotaped Deposition of Michael J. Ram; Subpoena, BLOM192.
Notice of Videotaped Deposition of Yvonne Fernandez, BLOM193.
Notice of Videotaped Deposition of Felix Jaory, BLOM194.
Notice of Videotape Deposition of Brett Nelson, BLOM195.
Notice of Videotaped Deposition of Norman Delgado, BLOM196.
Notice of Videotaped Deposition of Mark Anderson, BLOM197.
Notice of 30 (b) (6) Deposition of Oasis Medical, Inc., BLOM198.
Notice of Taking Videotaped Deposition of John J. Weidenbenner; Subpoena, BLOM199.
Notice of Taking Videotaped Deposition of Stephen J. Hilmes; Subpoena, BLOM200.
Corrected Subpoena to John J. Weidenbenner, BLOM201.
B&L's Objections to Notice of Deposition and Subpoena of Hans Hellenkamp, BLOM202.
Response and Objections of Non-Party Hans Hellenkamp to Defendant's Subpoena for Deposition and Production and Production of Documents, BLOM203.
B&L's Third Set of Requests for Production to Defendant, BLOM204.
Response and Objections of Non-Party Eric Weinberg to Defendant's Subpeona for Production of Documents, BLOM205.
Amended Notice of Videotaped Deposition of Brett Nelson, BLOM206.
Amended Notice of Videotaped Deposition of Michael J. Ram, BLOM207.
Notice of Subpoena Duces Tecum to Micra USA, Inc., BLOM208.
B&L's Second Set of Requests for Admissions to Defendant, BLOM209.
B&L's Second Set of Interrogatories to Defendant, BLOM210.
B&L's Fourth Set of Requests for Production to Defendant, BLOM211.
Complaint for Patent and Trademark Infringement; Summons; *Bausch & Lomb Surgical, Inc.* vs. *Visionar, Inc. and Med-Logic, Inc.*, U.S. Disctict Court for the Central District of California, Case No. SACV 00-412 DOC (ANX), BLOM213.
Dismissal Under FRCP Rule 41(a) (1); *Bausch & Lomb Surgical, Inc.* vs. *Visionar, Inc. and Med-Logic, Inc.*,, U.S. District Court for the Central District of California, Case No. SACV 00-412 DOC (ANX), BLOM214.
Moria, "Carriazo Barraquer Lamellar System for Keratoplasty" Brochure, V1, BLOM215.
Moria, "Carriazo Barraquer Lamellar System for Keratoplasty" Brochure, V2, BLOM216.
Moria, "Carriazo-Barraquer LSK" Brochure, 1998, V1, BLOM217.
Moria, "Carriazo-Barraquer LSK" Brochure, 1998, V2, BLOM218.
Order Granting Stipulation for Filing of Second Amended Complaint, Additional Depostitions, and Modifications of Case Management Schedule, Including Unsigned Second Amended Complaint, BLOM219.
Notice of Subpoena Duces Tecum to Moria USA, BLOM220.
Amended Notice of Videotaped Deposition of Mark Anderson, BLOM221.
Amended Notice of 30 (b) (6) Deposition of Defendant Oasis Medical, Inc., BLOM222.

Amended Notice of Videotaped Deposition of Norman Delgado, BLOM223.
Amended Notice of Videotaped Deposition of Yvonne Fernandez, BLOM224.
Plaintiff Bausch & Lomb Surgical, Inc.'s Responses to Second Set of Requests for Documents and Things, BLOM225.
Defendant's Responses to B&L's Fourth Set of Requests for Production of Documents (Set No. Four), BLOM226.
Defendant's Answer to Second Amended Complaint and Counterclaims, BLOM227.
Defendant's Responses to B&L's Second Set of Requests for Admissions (Nos. 73-185), BLOM228.
Defendant's Responses to B&L's Fourth Set of Requests for Production of Documents (Set No. Four), BLOM229.
Defendant's Responses to B&L's Second Set of Interrogatories (Nos. 13-15), BLOM230.
Notice of Continuation of Videotaped Deposition of Norman Delgado and as 30 (b) (6) Deponent for Categories 1-9, 12, 14-17, 24, 26, 27, and 30, BLOM231.
Amended Notice of Videotaped Deposition of Yvonne Fernandez, Individually, and as 30 (b) (6) Deponent for Categories 13, 28, and 29, BLOM232.
Amended Notice of 30 (b) (6) Deposition for Categories 18-23, William Hagel Designated Deponent, BLOM233.
Defendant's Second Set of Requests for Admissions to B&L (Nos. 29-89), BLOM234.
Defendant's Second Set of Interrogatories to B&L (No. 20), BLOM235.
Defendant's Third Set of Requests for the Production of Documents and Things to B&L (Nos. 201-250), BLOM236.
Defendant's First Supplemental Initial Disclosures, BLOM237.
Notice of Taking Videotaped Deposition of Gregory M. Hasley, BLOM238.
Notice of Taking Videotaped Deposition of Craig Larson, BLOM239.
Defendant's Amended Answer to Second Amended Complaint and Counterclaims, BLOM240.
Notice of Deposition of Plaintiff Bausch & Lomb Surgical, Inc. (Fed. R. Civ. P. 30 (b) (6) ), BLOM241.
B&L's Fifth Set of Requests for Production to Defendant, BLOM242.
B&L's Third Set of Interrogatories to Defendant, BLOM243.
B&L's Third Set of Requests for Admissions to Defendant, BLOM244.
B&L's Objections to Defendant's Notice of Taking Videotaped Deposition of Craig Larson, BLOM245.
Defendant's Third Set of Interrogatories to B&L (Nos. 21-25), BLOM246.
Defendant's Fourth Set of Requests for the Production of Documents and Things to B&L (Nos. 251-297), BLOM247.
Defendant's Second Supplemental Initial Disclosures, BLOM248.
B&L's Objections to Defendant's Notice of Deposition of Plaintiff Bausch & Lomb Surgical, Inc. (Fed. R. Civ. P. 30 (b) (6) ), BLOM249.
Defendant's Notice of Ex Parte Application for an Order Compelling the Attendance of Gregory Hasley at a Deposition, BLOM250.
Notice of Filing Under Seal Defendant's Memorandum of Points and Authorities, Ben Davidson's Second Declaration in Support of Defendant's Notice of Ex Parte Application for an Order Compelling the Attendance of Gregory Hasley at a Deposition, BLOM251.
First Declaration of Ben M. Davidson in Support of Defendant's Notice of Ex Parte Application for an Order Compelling the Attendance of Gregory Hasley at a Deposition, BLOM252.
Declaration of Bradley J. Sparks in Support of Defendant's Ex Parte Application for and Order Compelling the Attendance of Gregory Hasley at a Deposition, BLOM253.
[PROPOSED] Order Granting Defendant's Ex Parte Application for an Order Compelling the Attendance of Gregory Hasley at a Deposition, BLOM254.
Appendix of Lexis and Westlaw Cases Cited by Defendant in its Memorandum of Points and Authorities in Support of Defendant's Ex Parte Application for an Order Compelling the Attendance of Gregory Hasley at a Deposition, BLOM255.
Defendant's Fourth (sic) Supplemental Initial Disclosures, BLOM256.
Notice of Deposition and Production of Documents of Non-Party Witness Russell Koepnick Pursuant to Subpoena Dated Sep. 25, 2003, BLOM257.
B&L's Notice of Motion and Motion to Strike and Dismiss the Allegations, Affirmative Defenses, and Counterclaims Asserted in Defendant's Answer to Second Amended Complaint and Counterclaims Pursuant to Fed. R. Civ. P. 12 and 15, and Authorities in Support Thereof, BLOM258.
Declaration of Gregory M. Hasley with Attached Exhibits in Support of B&L's Motion to Strike and Dismiss the Allegations, Affirmative Defenses, and Counterclaims Asserted in Defendant's Answer to Second Amended Complaint and Counterclaims, BLOM259.
Notice of Deposition and Production of Documents of Non-Party Witness Alok Nigam Pursuant to Subpoena Dated Sep. 26, 2003, BLOM260.
Amended Proof of Service of Ex Parte Docs Filed Sep. 24, 2003, BLOM261.
B&L's Opposition to Defendant's Ex Parte Application for an Order Compelling the Attendance of Gregory Hasley at a Deposition, BLOM262.
Declarations of Jay C. Gandhi and Gregory M. Hasley In Opposition to Defendant's Ex Parte Application for an Order Compelling the Attendance of Gregory Hasley at a Deposition, BLOM263.
Evidentiary Objections and Motion to Strike by B&L to the First Declaration of Ben M. Davidson in Opposition to Defendant's Ex Parte Application for an Order Compelling the Attendance of Gregory Hasley at a Deposition, BLOM264.
Evidentiary Objections and Motion to Strike by B&L to the Declaration of Bradley J. Sparks in Opposition to Defendant's Ex Parte Application for an Order Compelling the Attendance of Gregory Hasley at a Deposition, BLOM265.
Civil Minutes—General: Defendant's Ex Parte Application for an Order Compelling the Attendance of Gregory Hasley at a Deposition is Denied, BLOM266.
Defendant's Request for Reconsideration ot the Denial of Its Ex Parte Application for an Order Requiring the Deposition of Gregory Hasley at a Deposition, BLOM267.
B&L's Sep. 30, 2003, Cumulative Amended Answers and Objections to Interrogatories 1-19, BLOM268.
Notice of Continued Deposition fo Eric Weinberg, BLOM269.
Notice of Videotaped Deposition of Fred Janette, BLOM270.
B&L's Brief and Declaration of Gregory M. Hasley in Opposition to Defendant's Request for Reconsideration of the Denial of Its Ex Parte Application for an Order Compelling the Attendance of Gregory Hasley at a Deposition, BLOM271.
Defendant's Notice of Ex Parte Application and Application for a Telephonic Scheduling Conference Regarding Bifurcation or Severance of Antitrust and Related Unfair Competition Counterclaims, BLOM272.
Memorandum of Points and Authorities in Support of Defendant's Ex Parte Application for a Telephonic Scheduling Conference Regarding Bifurcation or Severance of Antitrust and Related Unfair Competition Counterclaims, BLOM273.
Declaration of Richard J. Codding in Support of Defendant's Ex Parte Application for a Telephonic Scheduling Conference Regarding Bifurcation or Severance of Antitrust and Related Unfair Competition Counterclaims, BLOM274.
Declaration of Ben M. Davidson in Support of Defendant's Memorandum of Points and Authorities in Support of Ex Parte Application for a Telephonic Scheduling Conference Regarding Bifurcation or Severance of Antitrust and Related Unfair Competition Counterclaims, BLOM275.
Appendix of Lexis and West Law Cases Cited by Defendant in Its Memorandum of Points and Authorities in Support of Defendant's Ex Parte Application for a Telephonic Scheduling Conference Regarding Bifurcation or Severance of Antitrust and Related Unfair Competition Counterclaims, BLOM276.

[PROPOSED] Order Granting Defendant's *Ex Parte* Application for a Telephonic Scheduling Conference Regarding Bifurcation or Severance of Antitrust and Related Unfair Competition Counterclaims, BLOM277.
B&L's Opposition to Defendant's *Ex Parte* Application for a Telephonic Scheduling Conference Regarding Bifurcation or Severance of Antitrust and Related Unfair Competition Counterclaims, BLOM278.
Notice of Taking Videotaped Deposition of David Clonts, BLOM279.
Notice of Subpoena for Production of Documents from Non-Party Witness Russell Koepnick, BLOM280.
Amended Notice of Videotaped Deposition of Fred Janette, BLOM281.
Second Amended Notice of Videotaped Deposition of Fred Janette, BLOM282.
Order Denying Defendant's *Ex Parte* Application for Telephonic Scheduling Conference Regarding Bifurcation or Severance of Antitrust and Related Unfair Competition Counterclaims, BLOM283.
Civil Minutes—General: Withdrawal of Order Dated Sep. 30, 2003, and Defendant's *Ex Parte* Application for an Order Compelling Attendance of Gregory Hasley at a Deposition is Denied Without Prejudice, BLOM284.
B&L's Responses to Defendant's Second Set of Interrogatories (No. 20), BLOM285.
B&L's Responses to Defendant's Third Set of Requests for Production of Documents and Things (Nos. 201-250), BLOM286.
B&L's Responses to Defendant's Second Set of Requests for Admissions (Nos. 29-89), BLOM287.
Notice of Taking Non-Party Deposition of Dr. Mitchell A. Jackson, BLOM288.
Notice of Subpoena *Duces Tecum* to Akin Gump Strauss Hauer & Feld, LLP, BLOM289.
Notice of Voluntary Dismissal of Counterclaims Pursuant to Rule 41 (a) (1) (i) Fed. R. Civ. P., BLOM290.
Amended Notice of Deposition and Production of Documents of Non-Party Witness Alok Nigam Pursuant to Subpoena Dated Sep. 26, 2003, BLOM291.
Notice of Filing Under Seal Defendant's Memorandum of Points and Authorities and Declaration of Ben M. Davidson in Support of Defendant's Opposition to B&L's Motion to Strike and Dismiss the Allegations, Affirmative Defenses, and Counterclaims Asserted in Defendant's Answer to Second Amended Complaint and Counterclaims Pursuant to Fed. R. Civ. P. 12 and 15, BLOM292.
Appendix of Lexis and West Law Cases Cited by Defendant in Its Opposition to B&L's Motion to Strike and Dismiss the Allegations, Affirmative Defenses, and Counterclaims Asserted in Defendant's Answer to Second Amended Complaint and Counterclaims Pursuant to Fed. R. Civ. P. 12 and 15, BLOM293.
Declaration of Ben M. Davidson in Support of Defendant's Opposition to B&L's Motion to Strike and Dismiss the Allegations, Affirmative Defenses, and Counterclaims Asserted in Defendant's Answer to Second Amended Complaint and Counterclaims Pursuant to Fed. R. Civ. P. 12 and 15, BLOM294.
Defendant's Responses to B&L's Fifth Set of Requests for Production of Documents to Defendant (Set No. Five), BLOM295.
Defendant's Responses to B&L's Third Set of Requests for Admissions (Set No. Three), BLOM296.
Defendant's Responses to B&L's Third Set of Interrogatories to Defendant (Set No. Three), BLOM297.
Objections by Non-Party Akin, Gump, Strauss, Hauer & Feld, L.L.P. and B&L to Defendant's Notice of Subpoena *Duces Tecum* and Requests for Production of Documents Contained Therein, BLOM298.
B&L's Response to Defendant's Third Set of Interrogatories (Nos. 21-25), BLOM299.
B&L's Responses to Defendant's Fourth Set of Requests for Production of Documents and Things (Nos. 251-297), BLOM300.
Notice of Withdrawal of B&L's Motion to Strike and Dismiss the Allegations, Affirmative Defenses, and Counterclaims Asserted in Defendant's Answer, BLOM301.
Stipulation for Temporary Stay in Order to Conduct Expedited Mediation; Proposed Order, BLOM302.
Order Granting Stipulation for Temporary Stay in Order to Conduct Expedited Mediation, BLOM303.
Civil Minutes—General : In Chambers Conference Call Discussing Status of Case, BLOM304.
Civil Minutes—General : In Chambers Settlement Conference Discussing Status of Case AND Settlement is Placed, BLOM305.
Final Judgment and Injunction, BLOM306.
Stipulation to Vacate Claim Construction Rulings Entered Jul. 18, 2001 and Jul. 19, 2002: Order, BLOM307.
Barraquer, Editor, "Refractive Keratoplasty (Compilation Of Reprints) vol. 1," Instituto Barraquer de America, Bogata, Columbia, Mar. 1970, BLOM308.
Buratta et al., Editors, "LASIK Principles and Techniques," SLACK Inc., Chs. 4, 6-7, 12-13, 23-24, 26-27, and 33, 1998, BLOM309.
Burrata et al., Editors, "LASIK Surgical Techniques and Complications," SLACK Inc., Chs. 4-8, and 13-20, 2000, BLOM310.
Gimbel et al., "LASIK Complications: Prevention and Management," SLACK, Inc., Chs. 3-5, and 9, 1999, BLOM311.
Machat, "Excimer Laser Refractive Surgery," SLACK Inc., Chs. 8, 10, 12, and Appendices, 1996, BLOM312.
MICROTECH, Inc., Moria LASIK "One" Microkeratome Product Information, Bate Stamp Nos. BLOA004553-BLOA004556, http://www.microtechinc.com.[1], BLOM313.
Moria, LASIK "One" Microkeratome Product Information, Bate Stamp No. BLOA017127, http://www.moria-surgical.com, (accessed Oct. 20, 2000), BLOM314.
Moria, LASIK "One" Microkeratome Product Information, Bate Stamp Nos. BLOA021123-BLOA021137, http://www.moria-surgical.com, (accessed Oct. 20, 2000), BLOM315.
Moria, "LSK ONE Instruction Manuel LSK-Classic "ONE" Microkeratome Head," Version ME-LSK-ONE-VA-Aug. 19, 1997, Bate Stamp Nos. OM20790-OM20826, 1997, BLOM316.
Moria, "LSK ONE Instruction Manual LSK-Classic "ONE" Microkeratome Head," Version ME-LKS ONE-VA-Aug. 19, 1997, Bate Stamp Nos. MORIA003830-MORIA003868, 1997. (Alternate Version), BLOM316A.
Moria, "LSK ONE Instruction Manual Part 2/2 *LSK-ONE Microkeratome Head and Accessories," Version ME-ONE-VA-Aug. 6, 2000, Bate Stamp Nos. MORIA000827-MORIA000852, 2000, BLOM317.
Moria, LSK One Microkeratome Product Brochure, Bate Stamp Nos. BL001108-BL001111, BLOM318.
Rozakis, "Refractive Lamellar Keratoplasty," SLACK Inc., 1994.[2], BLOM319.
Singer, "Adjustable Power and Positioning Options Defined New Microkeratome," Ocular Surgery News, vol. 16, No. 21, Nov. 1, 1998, Reprinted by SLACK Inc., 1998, BLOM320.
Singer, "Adjustable Power and Positioning Options Defined New Microkeratome," Ocular Surgery News, vol. 16, No. 21, Nov. 1, 1998, Reprinted by SLACK Inc., 1998. (Alternate Version), BLOM320A.
Barker et al., "Keratophakia and Keratomileusis," International Ophthalmology Clinics, vol. 28, No. 2, pp. 126-132, Summer 1988. (Incomplete), 1 001902-001906.
Barraquer, "Keratomeleusis," International Surgery, vol. 48, No. 2, pp. 103-117, Aug. 1967. (Incomplete), 1 001893-001901.
Barraquer, "Lamellar Keratoplasty (Special Techniques)," Annals of Ophthalmology, pp. 437-469, Jun. 1972. (Complete), 1 001932-001953.
Barraquer, "Queratomileusis y Queratofaquia," 1980, 2 004176-004446.
Barraquer, "Keratomileusis for Myopia and Aphakia," Ophthalmology, vol. 88, No. 8, pp. 701-708, Aug. 1981, 1 001956-001964.
Barraquer, "Results of Hypermetropic Keratomileusis, 1980-1981," Steinway Instrument Co., pp. 25-44, 1 001971-001992.
Bores Eye Institute, "Lamellar Refractive Keratoplasty," Ch. 4, pp. 1-9, 1988, 1989, 2 004092-004101.
Burillon et al., "Combined Epikeratoplasty and Homoplastic Keratophakia for Correction of Aphakia: Double Curve Effect," Refractive & Corneal Surgery, vol. 9, pp. 214-218, May/Jun. 1993, 1 001965-001970.

Casebeer et al., "Lamellar Refractive Surgery," SLACK Inc., Ch. 3, pp. 41-56, 1996, 1 001752-001769.

Chiron Intraoptics, Refractive Surgery Catalog, 1992, 1 001772-001785.

Chiron Vision Corp., "Automatic Corneal Shaper™ Operator's Manual," Rev. 1.4, Jul. 1994, 1 002820-002854.

Clayman et al., "Intraocular Lens Implantation Techniques and Complications," The C.V. Mosby Company, p. 38, 1983, 1 000631-000634.

Draeger, "A Semi-Automatic Electric Keratome for Lamellar Corneal Graft," Klin. Mbl. Augenheilk, 167, pp. 353-359, 1975, 2 004085-004091.

Draeger et al., "New Methods in Refractive Corneal Surgery—An Experimental Study," Klin. Mbl. Augenheilk, 192, pp. 458-461, 1988, 2 004081-004084.

G&G Medical Instruments, Ltd., The MARINOFF Calibration-Inspection RK Microscope, Advertisement, 1 001770-001771.

Hanna et al., "Keratotomy for Astigmatism Using an Arcuate Keratome," Archives of Ophthalmology, vol. 111, No. 7, pp. 998-1004, Jul. 1993. (Abstract Only), 1 000168-000170.

Hanna et al., "Keratotomy for Astigmatism Using an Arcuate Keratome," Archives of Ophthalmology, vol. 111, No. 7, pp. 998-1004; Jul. 1993, 1 000171-000179.

Hofmann et al., "An Independent Evaluation of Second Generation Suction Microkeratomes," Refractive & Corneal Surgery, vol. 8, No. 5, pp. 348-354, Sep./Oct. 1992. (Abstract Only), 1 000150-000152.

Hofmann et al., "An Independent Evaluation of Second Generation Suction Microkeratomes," Refractive & Corneal Surgery, vol. 8, No. 5, pp. 348-354, Sep./Oct. 1992, 1 001796-001794.

Jones, "The Optical Micrometer," Optical Engineering, vol. 15, No. 3, pp. 247-250, May/Jun. 1976, 1 002855-002859.

Kohlhass et al., "Keratomileusis With a Lamellar Microkeratome and the Eximer Laser," Ophthalmologe, 92 (4):499-502, Aug. 1995. (Abstract Only), 1 000148-000149.

Kremer, "ALK-E: As Good as Advertised," Review of Ophthalmology, Aug. 1994, 1 001954-001955.

Kronemyer, "Advanced Microkeratome Simplifies ALK," Slack Inc., Jan. 1996, 1998, 1 000627-000630.

Microtech, Inc., Video Newsletter, vol. 1, Issue 2, Spring 1995, 1 001914-001915.

Nordan, "Keratomileusis," Refractive Keratoplasty, pp. 7-12, 1987, 1 001888-001892.

Pallikaris et al., "Excimer Laser in Situ Keratomileusis and Photorefractive Keratectomy for Correction of High Myopia," Journal of Refractive & Corneal Surgery, vol. 10, pp 498-510, Sep./Oct. 1994. (Incomplete), 1 001919-001931.

Pouliquen et al., "The Hanna Radial Microkeratome: Presentation and First Experiment," Dev. Ophthalmology, 14:132-136, 1987. (Abstract Only), 1 000153-000154.

Rozakis, editor, "Refractive Lamellar Keratoplasty," SLACK Inc., Chs. 1-2, 5-10, and 13, 1994, 1 001795-001887.

Ruiz, "Flap and Zap: Is The Next Radial K?," Review of Ophthalmology, Aug. 1994, 1 001916-001918.

Smith, "SCMD Keratome Unit," Refractive & Corneal Surgery, vol. 6, p. 207, May/Jun. 1990, 1 002860-002862.

Steinway Instrument Company, Inc., "The Steinway/Barraquer In-Situ Microkeratome Set," Brochure, 2 004072-004080.

Stonecipher et al., "Refractive Corneal Surgery with the Draeger Rotary Microkeratome in Human Cadavar Eyes," Journal of Refractive & Corneal Surgery, 10(1) :49-55, Jan./Feb. 1994. (Absract Only), 1 000145-000147.

Stortz Instrument Company, Eye Instrument Catalog, Twelfth Ed., 1973, 1 000652-000656.

U.S. District Court for the Eastern District of Pennsylvania, Civil Docket for Case No.: 99-CV-4247, *Bausch & Lomb et al.* v. *Moria S.A. et al.*, 2003, 3 004606-004616.

U.S. District Court for the Central District of California, Civil Docket for Case No.: 00-CV-11298, *Bausch & Lomb Inc.*, v. *Oasis Medical Inc.*, 2003, 3 004617-004635.

Wilson et al., "Corrective Measures for Myopia," Survey of Ophthalmology, vol. 34, No. 4, pp. 294-304, Jan./Feb. 1990. (Incomplete), 1 001907-001913.

Phoenix Keratek, Inc., "The Solution", Advertisement, Bate Stamp No. KOEPNICK000073.

Phoenix Biomedical, Inc., "Check Us Out!", Advertisement, Bate Stamp No. KOEPNICK000087.

Phoenix Biomedical, Inc., "Universal Keratome Model 1000", Advertisement, Bate Stamp No. KOEPNICK000088.

Phoenix Keratek, Inc., Product Brochure, Bate Stamp No. KOEPNICK000089 - KOEPNICK000095.

Binder, et al., "Comparison of the UniversalKeratome and the Automated Corneal Shaper," J Cataract Refract Surg-vol. 22, Nov. 1996, Bate Stamp No. KOEPNICK000096 - KOEPNICK000107 (missing pp. 1186-1187).

Binder, Video Presentation, Bate Stamp No. KOEPNICK000108 - KOEPNICK000130.

Updegraff, "Exploring Microkeratome Evolution and Design", Vision Surgery & Laser Ct., pp. 7-9, Bate Stamp No. KOEPNICK000133 - KOEPNICK000135.

Kronemyer, "Advanced Microkeratome Simplifies ALK", Ocular Surgery News; Bate Stamp No. KOEPNICK000136.

"News & Trends", Review of Opthalmology, Dec. 1995, Bate Stamp No. KOEPNICK000317 - KOEPNICK000139.

Schneider, "Eye Device Hits Market", Arizona Business Gazette, vol. 116, No. 5, Week of Feb. 1-7, 1996, pp. 1 and 15, Bate Stamp No. KOEPNICK000140 - KOEPNICK000141.

Binder, "Comparing Keratomileusis in Situ and Excimer Laser Assisted Keratomileusis in Situ", Refractive Business Advisor, Apr./May 1996, Bate Stamp No. KOEPNICK000142-145.

Littlefield, et al., "New Method for Reshaping the Cornea", Journal of Biomedical Optics, vol. 2, No. 1, pp. 106-114, Jan. 1997, KOEPNICK000147-KOEPNICK000156.

Kronemyer, "Advanced Microkeratome Simplifies ALK", Ocular Surgery News, Jan. 1996, Bate Stamp No. KOEPNICK000157 - KOEPNICK000159.

Lipner, "Microkeratomes: Exploring Current Technology", Eye World, Oct. 1966, pp. 39-40, Bate Stamp No. KOEPNICK000160 - KOEPNICK000161.

Singer, "1998 Guide to Microkeratomes- Demand Drives Growth in Microkeratome Market", Bate Stamp No. KOEPNICK000162 - KOEPNICK000164.

* cited by examiner

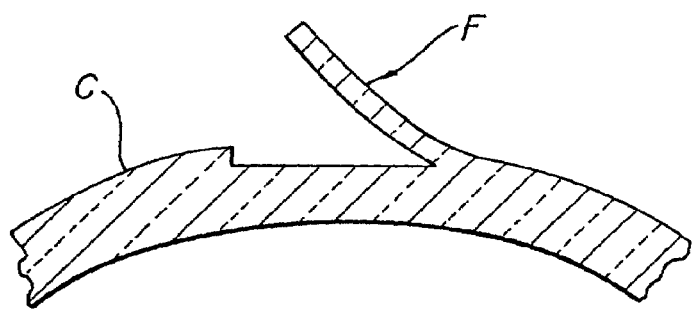
FIG. 1
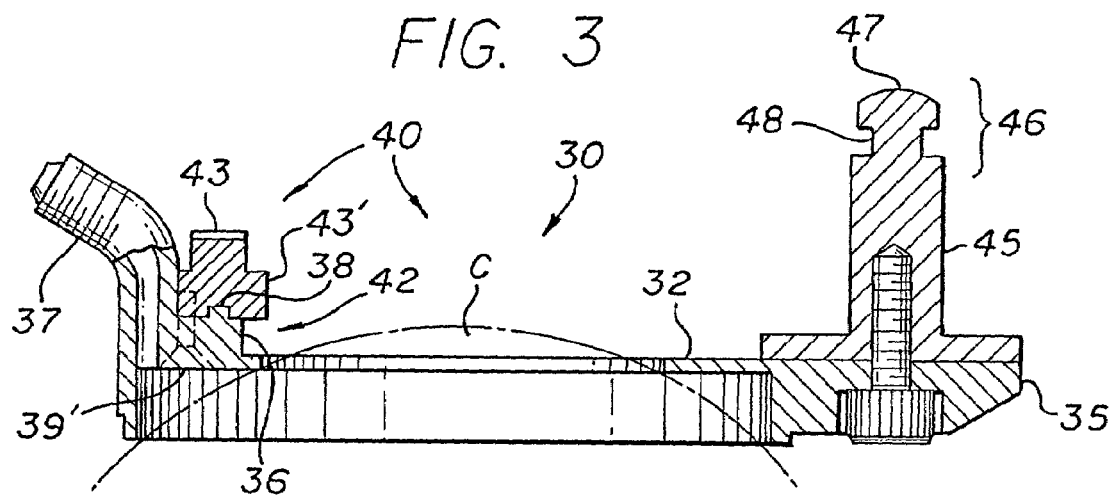
FIG. 3
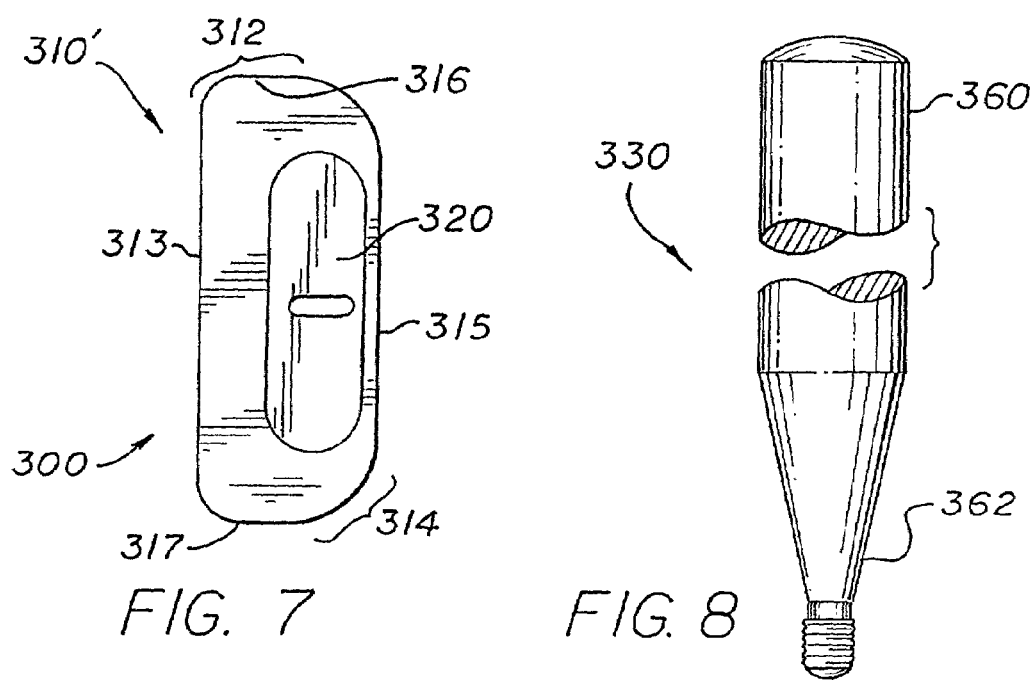
FIG. 7
FIG. 8

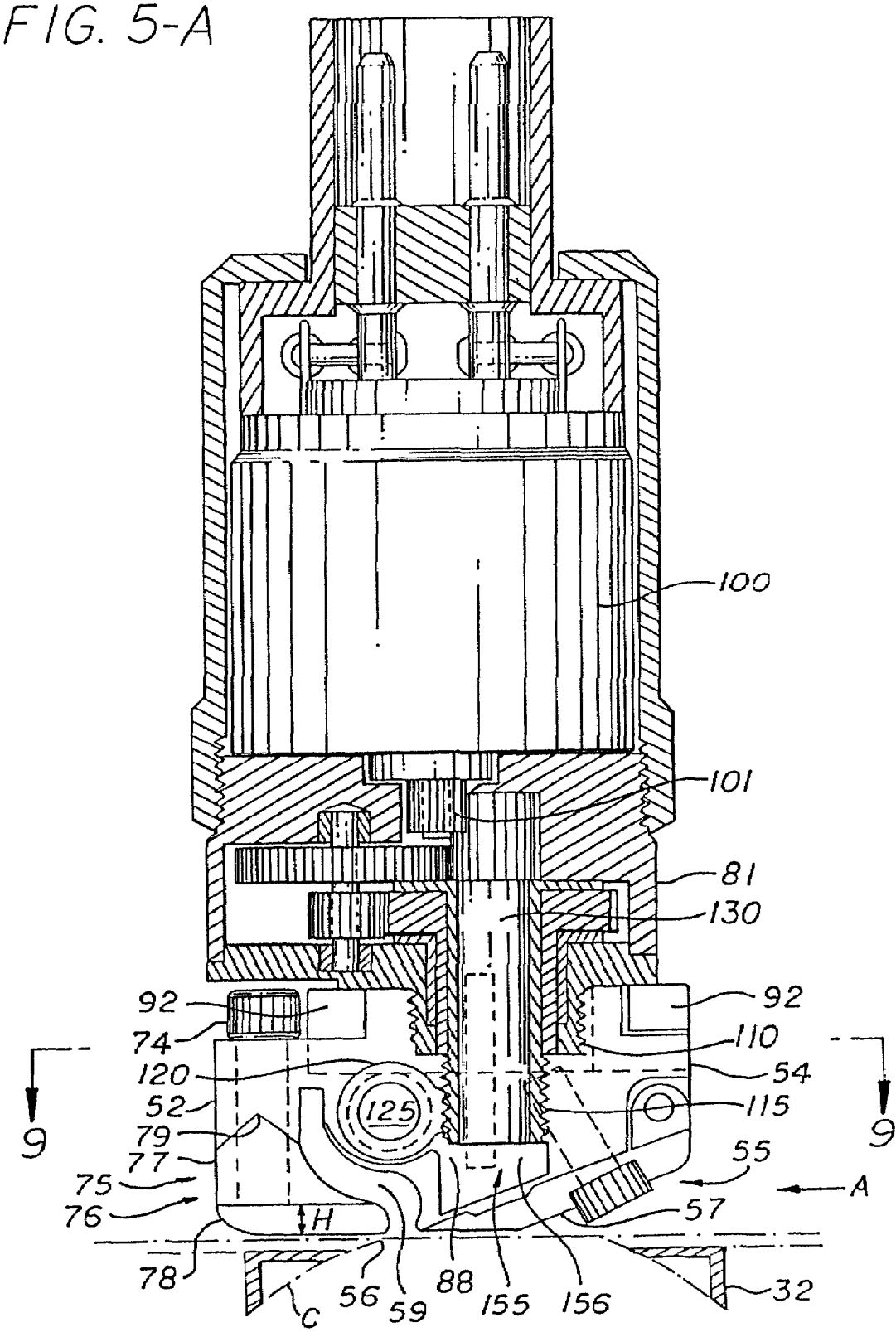
FIG. 5-A

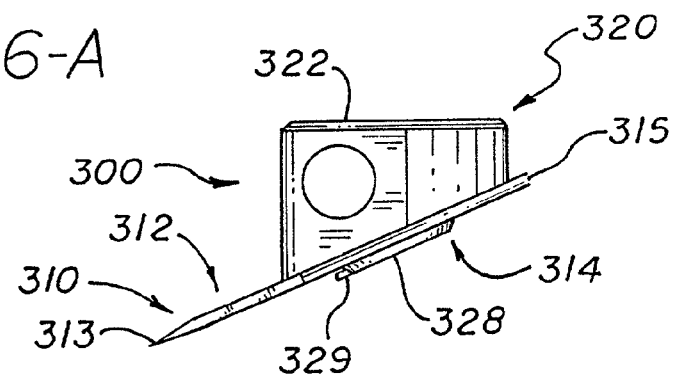
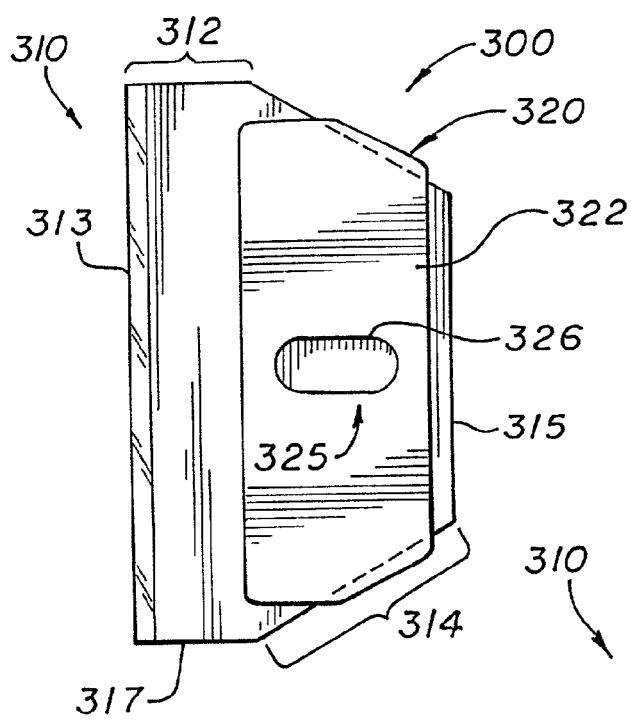
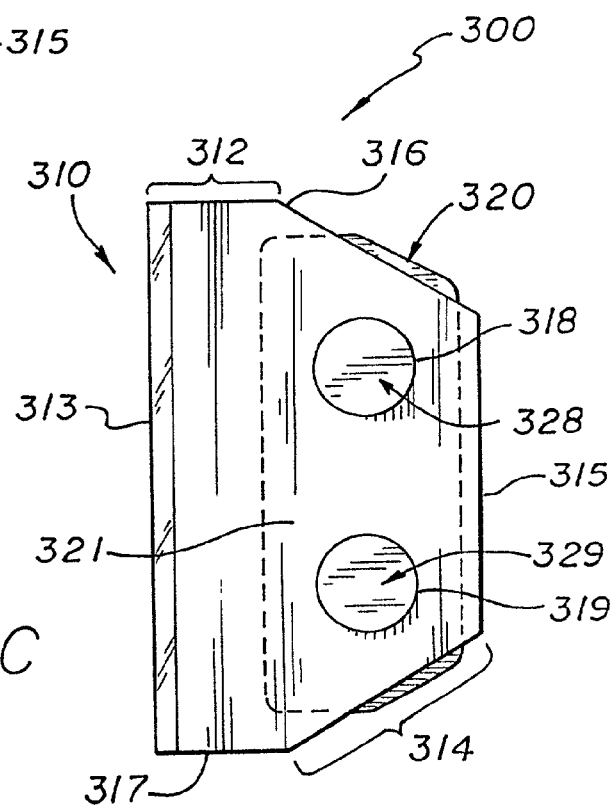

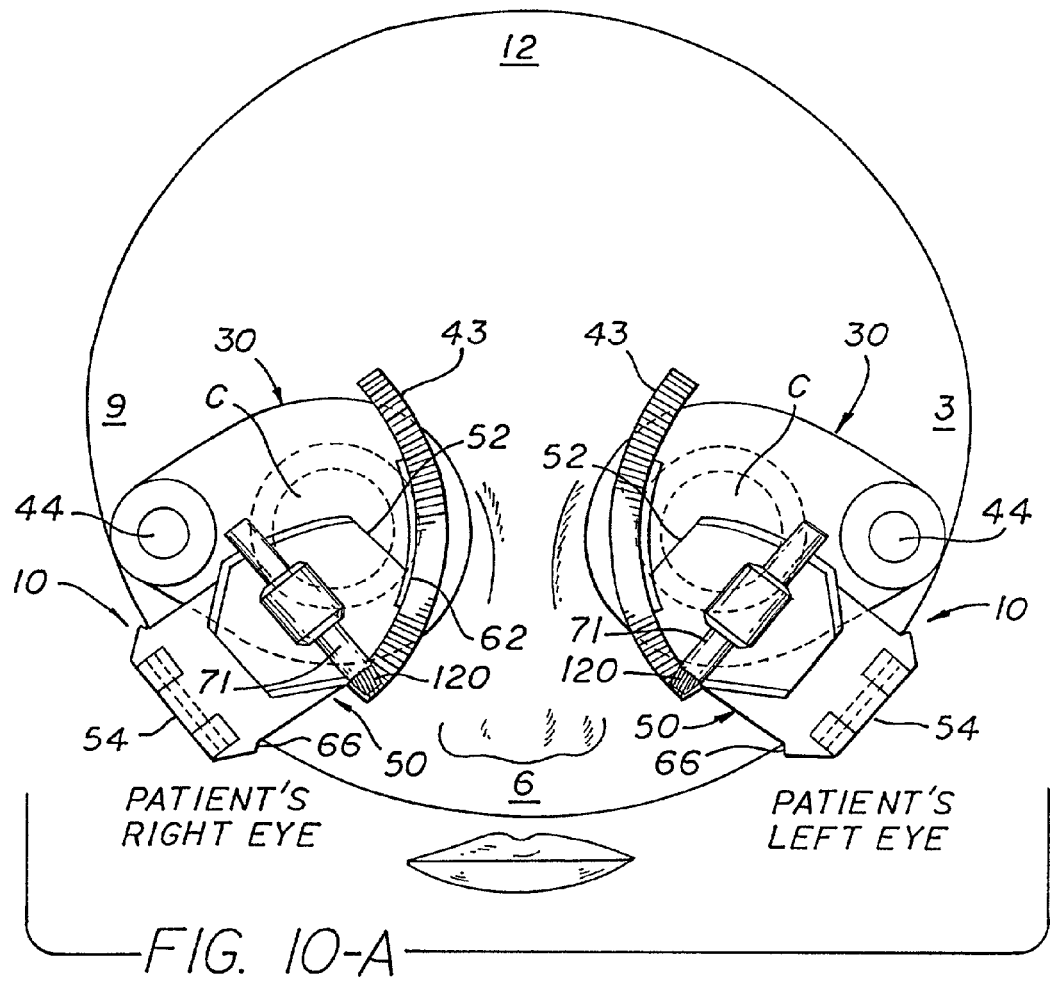
FIG. 10-A
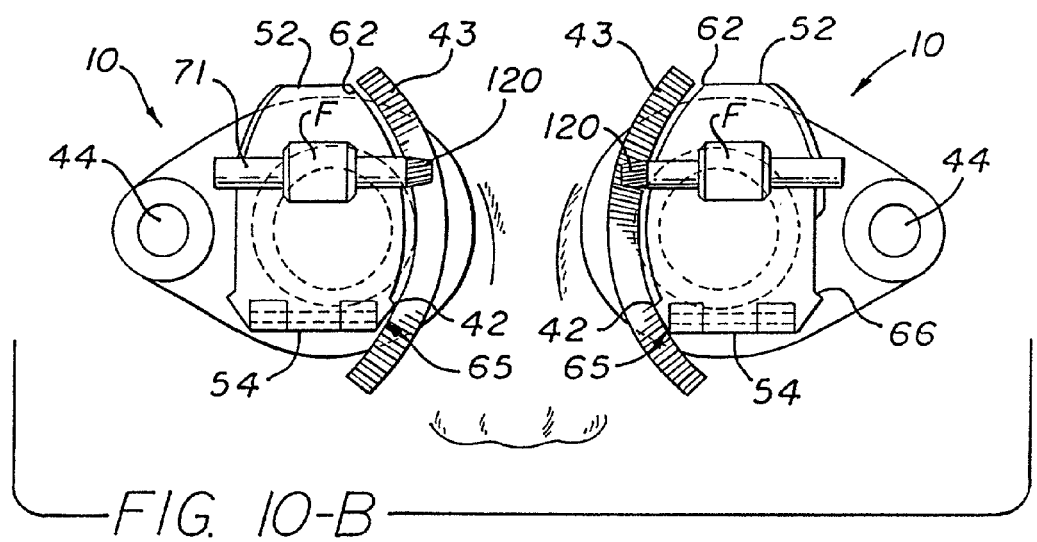
FIG. 10-B

AUTOMATIC SURGICAL DEVICE AND CONTROL ASSEMBLY FOR CUTTING A CORNEA

The present application is a continuation-in-part of and claims priority to the following applications and/or issued patents, each of which is incorporated fully herein by reference: U.S. patent application having Ser. No. 09/841,165 filed Apr. 24, 2001, now abandoned which is a continuation of an earlier filed U.S. patent application, namely Ser. No. 08/840,430 filed on Apr. 29, 1997 which matured into U.S. Pat. No. 6,296,649 on Oct. 2, 2001, which itself was a continuing application based on that U.S. patent application filed on Feb. 7, 1996 and assigned Ser. No. 08/598,180 which matured into U.S. Pat. No. 5,624,456 on Apr. 29, 1997. The present application also claims priority to and is a continuation-in-part of the following, each also incorporated fully herein by reference: a U.S. patent application filed on Apr. 24, 1998 and assigned Ser. No. 09/065,848 which matured into U.S. Pat. No. 6,007,553 on Dec. 28, 1999, which itself was a Continuation-In-Part application of an earlier filed U.S. patent application, namely, Ser. No. 08/845,171 filed on Apr. 25, 1997 which matured into U.S. Pat. No. 6,051,009 on Apr. 18, 2000. The present application further claims priority to and is a continuation-in-part of the following, each also being incorporated fully herein by reference: a U.S. patent application filed on Oct. 17, 2000 and assigned Ser. No. 09/690,204, now U.S. Pat. No. 6,605,099, itself a continuing application of an earlier filed U.S. patent application filed on Nov. 4, 1999 and assigned Ser. No. 09/433,478 which issued a U.S. Pat. No. 6,132,446 on Oct. 17, 2000; and finally, a U.S. patent application filed on Nov. 4, 1999 and assigned Ser. No. 09/433,479 now U.S. Pat. No. 6,527,788.

BACKGROUND OF THE INVENTION

1. Field of the Invention

The present invention relates to an improvement in a medical apparatus used during the performance of eye surgery, and more specifically, towards an automatic surgical device for cutting the cornea of a patient's eye and creating a hinged flap of corneal tissue. Moreover, the present invention is directed towards an improved cutting blade assembly to be used in conjunction with a cutting head assembly of the automatic surgical device, and a control assembly for use therewith which is capable of shutting off power supplied to the device when problems are encountered during the surgical cutting of the cornea.

2. Description of the Related Art

Until about twenty years ago, refractive errors of light passing through the eye could only be treated with eyeglasses or contact lens, both of which have well known disadvantages for the user. Consequently, in the last several years, research has been directed to surgical operations to change the refractive condition of the eye, i.e., either to flatten or increase the curvature of a patient's eye depending upon his or her condition. The desired result of such surgical operations is that light rays passing through the cornea will be refracted to converge properly and directly onto the retina so as to allow a patient to clearly see close or distant images.

Automated Lamellar Keratectomy (ALK) is one surgical technique developed wherein the eye is first numbed by a drop of anesthetic, and then a suction ring is placed on the eye to carefully position the cornea (termed "centration" in the art) for being cut by a very fine microsurgical instrument known as a microkeratome. The microkeratome is generally a blade carrying device that must be manually pushed or mechanically driven in a cutting path across the suction ring simultaneous with the motorized movement of the cutting element, which movement is transverse to the direction of the cutting path. For treating myopia pursuant to ALK procedures, the microkeratome is typically used to first cut into the cornea so as to raise and separate a thin layer of the anterior cornea of between 100–200 microns in depth and about 7 millimeters in diameter. Next, the microkeratome is then used to make a second pass over the cornea to resect or remove a smaller part of the cornea, generally about 4 to 6 millimeters in diameter, which is then discarded. The anterior corneal cap which was cut away with the first pass of the microkeratome is then put back into its original position, without suturing, for healing to occur. The desired result of this procedure is that the cornea will have a new curvature because of the resected tissue, which provides a new refracting surface to correct the patient's original myopic condition. To correct hyperopia under ALK however, the microkeratome is typically used to make a single deep pass over the cornea. The cut layers are put back into their original position, without any removal of any other tissue. Because of the depth of the cut, the intraocular pressure within the eye causes a steepening of the cornea to again, provide a new refracting surface which hopefully will correct the patient's original hyperopic condition.

Another more recent advance in surgical procedures to correct refractive errors of the eye involves the introduction of laser procedures. One such procedure, known as Laser Intrastromal Keratomileusis, (LASIK), is currently considered optimal because it allows sculpting of the cornea by a laser, without damaging adjacent tissues. Moreover, with the aid of computers, the laser can be programmed by a surgeon to precisely control the amount of tissue removed, and significantly, to permit more options for the reshaping of the cornea. Under LASIK procedures, the eye is still typically positioned within a suction ring and a microkeratome is typically used to cut into the cornea so as to raise a thin layer of the cornea.

In recent years, it has been learned that regardless of whether ALK or LASIK surgery is performed, the microkeratome which cuts the cornea should not create a corneal cap nor separate the cut corneal tissues completely from the rest of the cornea. The reasons are primarily two-fold: first, the possibility exists that when the corneal cap is put back in place on the cornea, it will not be aligned properly with the remaining corneal tissues, which has several drawbacks for the patient, and second, the possibility exists that the corneal cap will become lost during the surgery, and if that occurs, the consequences for the patient are catastrophic. In great part to overcome these problems, among others, the inventor of the invention described in the present application created and developed an improved surgical device for cutting the cornea which automatically and reliably leaves a portion of the raised and separated corneal tissues connected or "hinged" to the eye, thereby forming a raised layer of corneal tissue hinged to the eye, known as a corneal flap F, illustrated in FIG. 1.

Significantly, it has been determined that the corneal flap should have a depth of no less than 130 microns and no more than 160 microns to yield optimal results. It should be borne in mind that achieving this result during surgery requires an extremely precise instrument as one micron is a unit of length equal to one thousandth of a millimeter. Further, it is desirable, if not imperative, for the microkeratome to cut across the cornea in a manner that will very finely and smoothly cut the corneal tissues. In this regard, there is a need in the art for improvement in that when the smoothness of a cut made to the cornea by known microkeratome devices is closely examined under a microscope, the cut, corneal tissue edges are seen to be a bit irregular, if not slightly jagged. It would be ideal if a microkeratome device were able to cut across the cornea, not only so as to cut and raise the microscopicly thin layer of corneal tissue currently considered optimal, but to do so in a manner which results in a noticeably improved cut to the cornea, namely, by yielding very fine, smooth and almost undetectable cut corneal tissue edges.

In addition, there is room for known microkeratome devices to be improved with regard to the assembly required prior to performing surgery on a patient's eye, as well as with regard to the disassembly, sterilization and cleaning of the device, or parts thereof, following surgery. Specifically, microkeratome devices, and particularly, the cutting blade housed therein, which penetrates into and cuts the cornea must be in a proper sanitary and sterilized state until generally about the moment when surgery on the eye is to begin. Known microkeratome devices, however, have required that the housing for the cutting blade be manipulated so as to create access to an interior thereof and permit the placement of the cutting blade therein, which itself must typically be handled as well, after which, the housing must again be manipulated so as to close off the access means, all of which has hopefully resulted in the cutting blade being properly in place. This excessive manipulation required of known microkeratome devices is not conducive, however, to maintaining the proper sanitary and sterilized state required for surgery. Moreover, in manipulating the access means of certain known microkeratome devices, some surgeons have unintentionally caused the cutting blade to become dislodged, or worse, have even bent the cutting blade, thereby requiring the assembly process to start over again. Further, the mechanisms within known microkeratome devices for holding the cutting blade have been designed for repeated use. This factor tends to only exacerbate the problems encountered in the art in that these known blade holding mechanisms should also be removed from the microkeratome device following a surgery in order to be properly cleaned and/or sterilized for subsequent use. The assembly and disassembly of these mechanisms are not only tedious and time consuming, but are fraught with the difficulties of maintaining sterilization and ensuring proper re-assembly.

Consequently, there is a need in the art for an improved microkeratome device for cutting the cornea of a patient's eye which can easily receive and which facilitates the proper positioning of a cutting blade therein, without excessive manipulation. There is also a need for an improved cutting blade assembly that facilitates easy insertion within a microkeratome device, with little danger of becoming bent, while simultaneously offering the user the knowledge that it is securely and properly in place. Any such improved cutting blade assembly should similarly be quickly and easily removed from the microkeratome device, and will preferably be disposable. It would be ideal if any such improved cutting blade assembly could be readily packaged in containers that permit sterilization prior to shipping, and which remain sterilized during shipping, and further, which could be easily removed from the sterile packaging for insertion into the microkeratome while maintaining sterility. In this regard, any such improved cutting blade assembly would ideally include an instrument which facilitates the removal of the assembly from a sterile container and the insertion thereof into the microkeratome, while maintaining sterility.

Known microkeratome devices are thought to have other, fairly significant deficiencies as well. For example, when a surgery on a patient's eye is underway, at times the suction or vacuum provided to temporarily attach the positioning ring to the cornea is either broken or interrupted. Given the precision cutting which is needed for such surgeries, however, it is highly undesirable, for the eye to continue to be cut during such situations. To date, known microkeratome devices continue cutting in such situations. Thus, it would be highly beneficial to provide an improved microkeratome device with a control assembly that could detect problems encountered during the surgical cutting of the cornea and that will shut off power supplied to the device when problems are detected so as to stop the cutting of the cornea by the microkeratome. Moreover, if surgery on a patient's eye is proceeding well, but there is sudden power loss, any such control assembly should enable the microkeratome device to continue functioning during the rather short duration of the operation, without interruption, both in terms of continuing to ensure a power supply to the device and a supply of vacuum to the positioning ring.

SUMMARY OF THE INVENTION

The present invention is designed to satisfy the needs which remain in the art of microkeratome devices used to cut the cornea of a patient's eye. In this regard, the present invention is directed towards an improved microkeratome which is able to cut and raise a microscopicly thin layer of corneal tissue in a manner that results in very fine, smooth and almost undetectable cut corneal tissue edges. Along these lines, the present invention is seen to include structure for retaining and positioning the eye on which surgery is to be performed, a cutting head assembly, including a cutting element positioned therein, for cutting the cornea of the eye, and in some embodiments a coupling member for detachably coupling the retaining and positioning means and cutting head assembly while permitting movement of the cutting head assembly relative to the retaining and positioning means along a generally arcuate path.

In a preferred embodiment, the retaining and positioning structure includes a positioning ring configured to achieve temporary attachment to a portion of the eye surrounding the cornea to be cut, and which exposes and presents the cornea for cutting. The positioning ring may include a guide assembly operably associated therewith and defining a generally arcuate path. Furthermore, the cutting head assembly of the present invention is structured and disposed to be cooperatively associated with the positioning assembly and to be driven substantially but not completely over the cornea of the eye so as to cut the cornea and form the corneal flap. The cutting head assembly is also, in at least one embodiment, structured and disposed to be guided by the guide assembly along a generally arcuate path during movement of the assembly thereacross. The cutting head assembly in the illustrated embodiment is seen to comprise a main housing which carries a cutting element positioned therein and disposed for cutting and raising the corneal flap. Moreover, in the preferred embodiment, the cutting head assembly includes a flap receiving gap formed within an undersurface thereof forward of the cutting element for protectively receiving the corneal flap of tissue formed by the forward movement of the cutting head assembly. Further, the cutting head assembly may be structured and disposed to be movably coupled to the positioning ring by way of a coupling member which detachably couples the cutting head assembly and the positioning ring and yet, permits movement of the cutting head assembly relative to the positioning ring along the generally arcuate path.

The present invention further comprises a driving assembly for driving the cutting head assembly over the retaining and positioning assembly, and in the preferred embodiment, may include a stop assembly, which is structured and disposed to limit movement of the cutting head assembly across the retaining and positioning assembly. The stop assembly may be formed on the cutting head assembly and may be structured and disposed to engagingly abut a portion of the guide assembly so as to limit further movement of the cutting head assembly at a point before the cutting element has passed completely over the cornea of the eye, thereby forming the corneal flap on the eye undergoing surgery. In the preferred embodiment, the drive assembly is operably connected to the cutting head assembly at a top surface thereof and is capable of stopping and reversing the direction of movement of the cutting head assembly once the stop assembly has prevented movement of the cutting head assembly in a first direction across the retaining and positioning assembly.

In addition, the present invention is directed towards an improved microkeratome cutting blade assembly that permits quick and easy installation and removal from the microkeratome housing, without excessive manipulation, and which provides an effective cut and range of movement. Preferably, the cutting blade assembly of the present invention is seen to comprise an improved cutting blade and blade holder. The cutting blade comprises a front portion that includes a sharp, forward cutting edge, a rear, trailing portion having a rear edge, and a pair of side edges, at least one of which extends and tapers between the front and rear trailing portions. The cutting blade, which may be secured to the blade holder in any operable method, may further include at least one aperture formed therein, and preferably, a pair of apertures disposed in the rear, trailing portion in substantially aligned relation with one another. Preferably, the cutting blade is substantially flat and made of stainless steel, with the front portion of the cutting blade having an overall dimension which is larger than the rear trailing portion. The blade holder of the improved cutting blade assembly is formed so that an underside thereof is secured to the cutting blade, such as at the at least one aperture on the cutting blade, and so that a top side of the blade holder includes structure for being operably driven by the drive assembly of the microkeratome device, which may comprise a recess formed within the blade holder. In the preferred embodiment, the blade holder will be molded of a plastic material and will be press fit during manufacture into the at least one aperture on the cutting blade so as to provide an integrally formed cutting blade assembly. In a most preferred embodiment, the cutting blade assembly of the present invention will additionally comprise a tool which facilitates the removal of the cutting blade and blade holder from a sterile packing container and the insertion thereof in a microkeratome device, while maintaining sterility.

The present invention is also directed towards a control assembly for a microkeratome device that is capable of detecting problems encountered during the surgical cutting of the cornea and either shutting off power supplied to the device, if appropriate, or ensuring that power and/or a vacuum continue to be supplied to the device, if appropriate.

The objects, features and advantages of the present invention will be more readily understood upon consideration of the accompanying drawings as well as the detailed description of a preferred embodiment(s) for the invention, set forth below.

BRIEF DESCRIPTION OF THE DRAWINGS

For a fuller understanding of the nature of the present invention, reference should be had to the following detailed description taken in connection with the accompanying drawings in which:

FIG. 1 is schematic illustration of a cornea of an eye wherein a corneal flap has been created.

FIG. 3 is a cross sectional view of the retaining and positioning means shown in FIG. 2.

FIG. 5-A is a partial cross sectional view of the preferred microkeratome in a partially disassembled state so as to illustrate the improved access means, without a cutting blade assembly inserted therein.

FIG. 6-A is a side view of the cutting blade assembly according to the present invention in a preferred embodiment.

FIG. 6-B is a top plan view of the cutting blade assembly illustrated in FIG. 6-A.

FIG. 6-C is a bottom view of the cutting blade assembly illustrated in FIG. 6-A.

FIG. 7 is a top plan view of the cutting blade assembly of the present invention in an alternative embodiment.

FIG. 8 is a side view of a tool which facilitates the removal of the cutting blade assembly shown in FIGS. 6 and 7 from a sterile packing container and the insertion thereof in a microkeratome device, while maintaining sterility.

FIG. 10-A is a front schematic illustration of the preferred microkeratome in use on both a patient's left and right eyes and illustrating the cutting head assembly in the initial position.

FIG. 10-B is a front schematic illustration of the preferred microkeratome illustrated in FIG. 10-A but depicting the cutting head assembly in the movement stopped position wherein a corneal flap has been formed with the resulting hinged portion being oriented so as to cooperate with the blinking of the eye following surgery.

Like reference numerals refer to like parts throughout the several views of the drawings.

DETAILED DESCRIPTION OF THE PREFERRED EMBODIMENT

Figure 2:
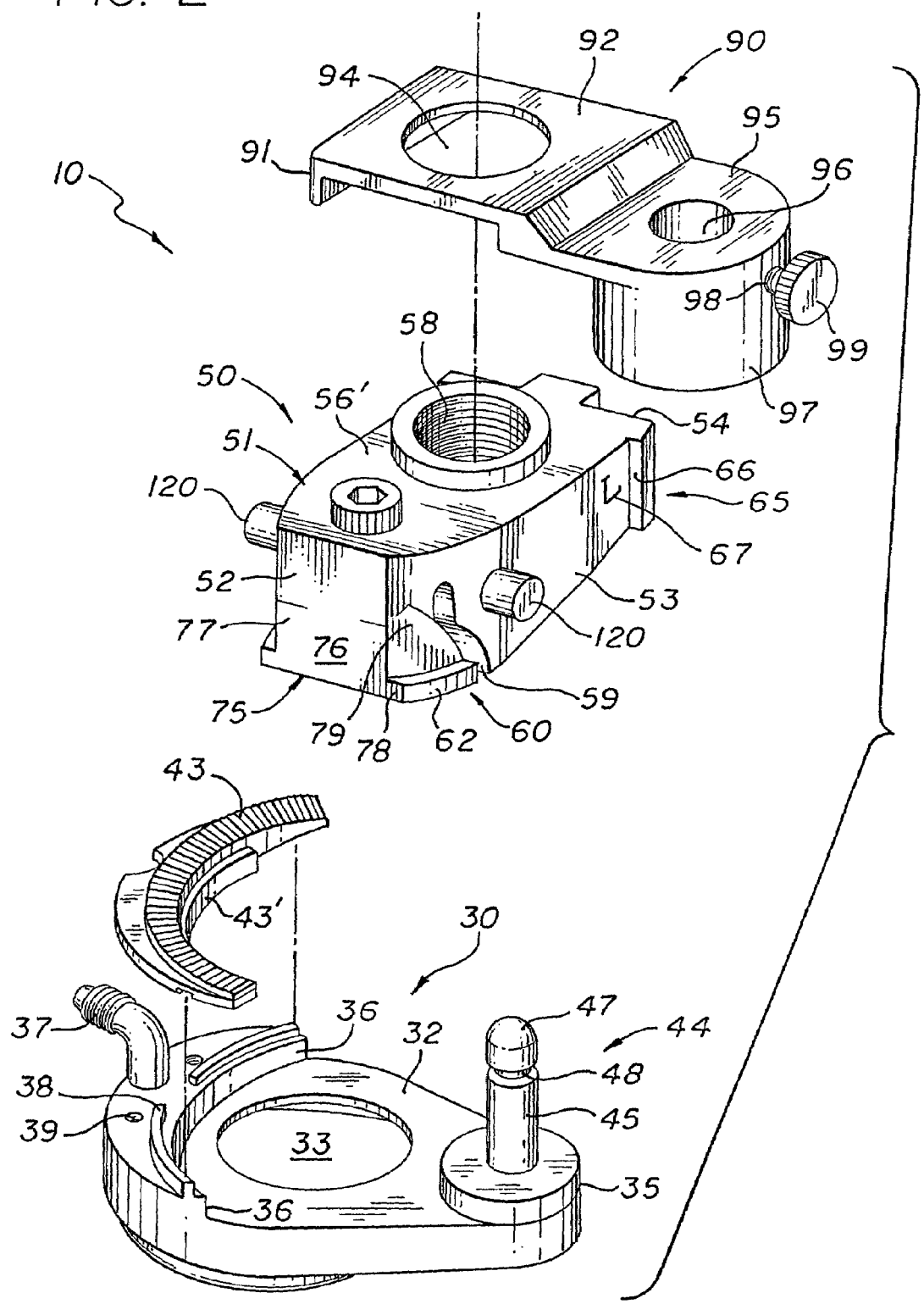
FIG. 2 is an exploded perspective view of a preferred microkeratome retaining and positioning means, of a preferred microkeratome cutting head assembly, as well as a preferred microkeratome coupling member according to the present invention.

As illustrated throughout the Figures, the present invention is directed towards an improved automatic microkeratome device for smoothly cutting the cornea of an eye, generally indicated by reference numeral 10, and towards a cutting blade assembly therefor, generally indicated by reference numeral 105, and towards a control assembly therefor, generally indicated by reference numeral 200.

The preferred and improved automatic microkeratome device of the present invention, which is structured to cut substantially but not completely across the cornea of a patient's eye so as to raise a thin layer thereof and create a hinged flap of corneal tissue, will be discussed first. As illustrated in FIGS. 2 and 3, the preferred microkeratome device 10 includes means 30 for retaining and positioning the eye on which surgery is to be performed. The retaining and positioning means 30, which may be made of high grade stainless steel, preferably comprise a positioning ring 32 having an aperture 33 formed therein. The aperture 33 is sized to permit the cornea C, of the eye to pass therethrough and be exposed, as depicted in FIG. 3. As illustrated, the positioning ring 32 is preferably defined by a generally tear-drop shape.

Figure 11:
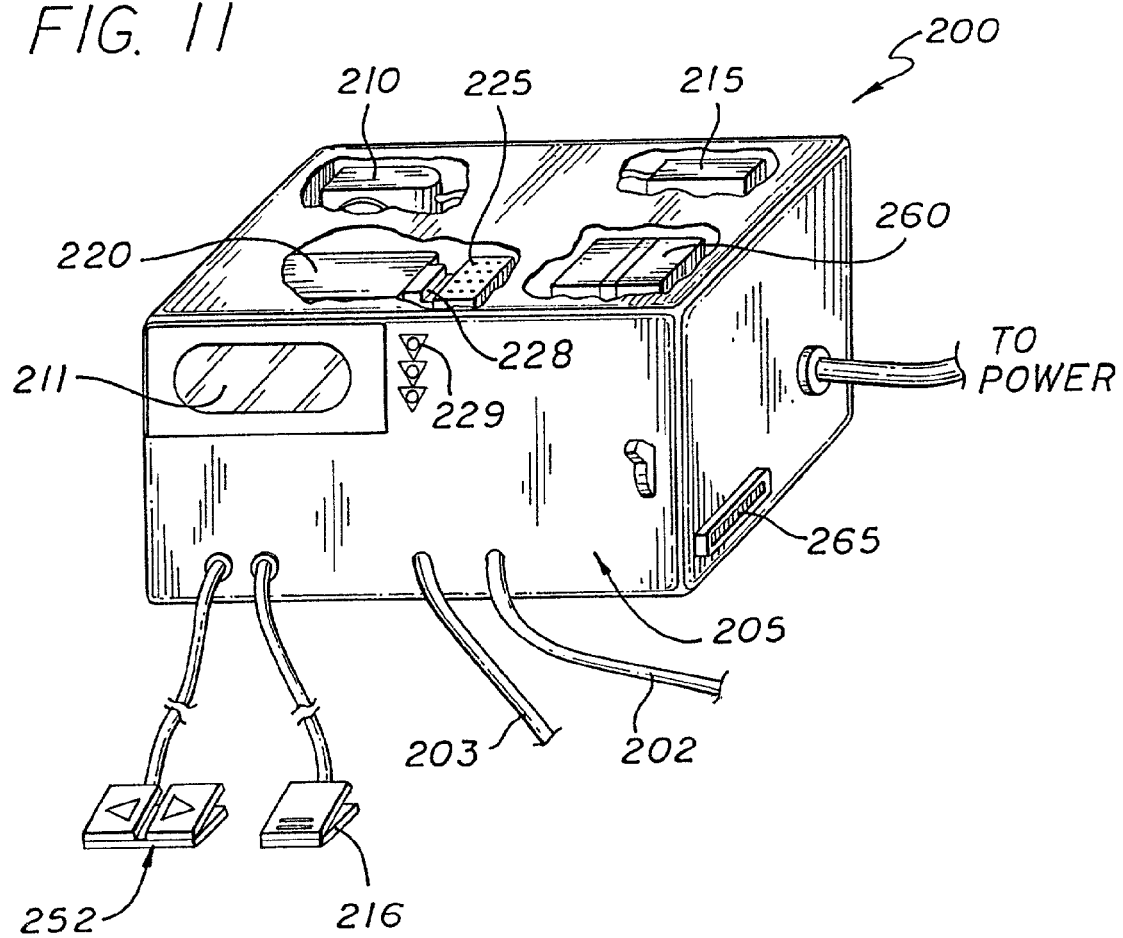
FIG. 11 is a perspective, partial cut away view of a preferred control assembly configuration according to the present invention which is to be used with a microkeratome device such as illustrated in FIG. 2.
Figure 12:
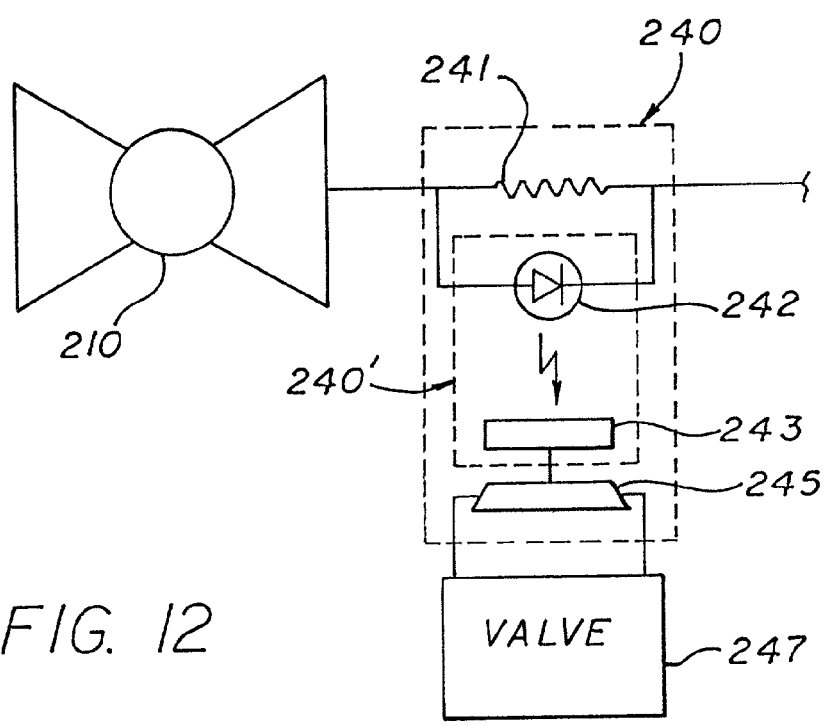
FIG. 12 is an isolated diagram of the configuration of a preferred optic coupler for the control assembly according to the present invention.

Positioning ring 32 further includes means for being temporarily attached to a portion of the eye surrounding the cornea on which surgery is to be performed. Ideally, the temporary attachment means include suctioning assembly. For example, positioning ring 32 preferably includes a connection member 37, which as illustrated in FIGS. 2 and 3, is in fluid communication with an undersurface of positioning ring 32. Connection member 37 is adapted to be interconnected with a vacuum hose 202, which as shown in FIG. 11, may be connected to a vacuum pump 210, such that when suction occurs, the undersurface of positioning ring 32 forms a seal about and is retained about the corneal portion of the eye which is about to undergo surgery. Further, the structure of positioning ring 32, accompanied by the suctioning, acts to properly position the cornea C, for surgery and to maintain the position during surgery as well. Typically, a vacuum of about 25 inches of Hg at sea level will be used.

The retaining and positioning means 30 further include a guide means or guide assembly 40 formed thereon, best illustrated in FIG. 3. Guide means 40 may be formed directly on the positioning ring 32, so as to be integral therewith, or may be operably connected thereto as a separate element. In any event however, the guide means 40 will be disposed on positioning ring 32 so as to guide and facilitate movement of the cutting head assembly 50, discussed below, during the surgical cutting of the cornea. Referring to FIG. 3, in the preferred embodiment, the guide assembly 40 are seen to comprise a channel member 42, which extends along a length of at least one side of positioning ring 32 and preferably, on an upper surface of positioning ring 32. It will also be appreciated from the drawings that channel member 42 extends across ring 32 in an arcuate or semi-circular path. In the most preferred embodiment channel member 42 is formed by the interconnection of two separate elements, namely, an upwardly and arcuately extending sidewall 36 formed on positioning ring 32, and a toothed track 43 which is interconnected with sidewall 36. Still referring to FIG. 3, in the most preferred embodiment, positioning ring 32 is seen to include the upwardly and arcuately extending sidewall 36 having a ridge 38 formed on an upper surface thereof, and extending partially if not completely along, at least one side of positioning ring 32. Further, in this preferred embodiment, the toothed track 43 is structured to be operably connected to ridge 38 by way of mating structure. For example, the mating structure can be in the form of a receiving groove disposed on the undersurface of toothed track 43, and/or by way of conventionally known fasteners 39' such as screws, rivets, etc. which may pass through positioning ring 32 at apertures 39 and extend into toothed track 43. As further illustrated in FIG. 3, toothed track 43 is seen to include a lip 43' which is sized and dimensioned to protrude beyond the vertical plane formed by sidewall 36. Thus, the guide assembly 40 in the form of a generally "C" shaped channel member 42 is comprised by the combined structure of sidewall 36 and toothed track 43, having lip 43'. It will be appreciated that toothed track 43 also cooperates with the drive assembly 80 (see FIGS. 4 and 9) so as to drive the cutting head assembly 50 across positioning ring 32, as more fully discussed below, and may be on an interior or the preferred exterior of the drive assembly 80.

The guide assembly 40 may further or alternately comprise a rigid upstanding member 44 disposed on the retaining and positioning means 30, and generally opposite the toothed track 43. As will again be appreciated from the drawings, in the preferred embodiment, wherein positioning ring 32 is of a tear-drop shape, rigid upstanding member 44 comprises a post member 45 securely connected to positioning ring 32 on an upper surface thereof at or near a tip 35 thereof. From the explanation which follows, it will become clear that in the preferred, illustrated embodiment, channel member 42 and rigid upstanding member 44 permit the cutting head assembly 50 of this invention to become effectively guided and securely received on the positioning ring 32 in two places while still permitting the cutting head assembly 50 to be smoothly and slidably moved over positioning ring 32 along a generally arcuate path, by way of a pivoting motion about rigid upstanding member 44.

Referring now to FIG. 2, the preferred microkeratome device is seen to include a cutting head assembly 50. A primary purpose of the cutting head assembly 50 is to house a cutting element 70 such as a cutting blade, see FIG. 5, with a cutting surface operatively exposed therefrom. As such, upon the cutting head assembly 50, with the cutting element 70 operatively disposed therein, being moved across the cornea retained within positioning ring 32, the cornea may be precisely cut by cutting element 70. To accomplish this, cutting head assembly 50 includes a main housing 51 containing the cutting element 70. Additionally, included in the main housing 51 is an aperture 58 structured and disposed to permit the drive assembly 80 to be operably connected thereto, such as from the preferred vertical orientation, (see FIGS. 4 and 9) and in the illustrated embodiment, to thereby drive the cutting head assembly 50 across positioning ring 32 in order to effectively cut the cornea. Further, as the cutting head assembly 50 must be driven in a smooth and controlled manner across the cornea, housing 51 includes a track assembly 60 which is structured and disposed for mating communication with and tracking within channel member 42, of positioning ring 32, in order to help precisely guide the cutting head assembly 50, and therefore the cutting element 70, along the defined arcuate path. Finally, as a feature of the preferred microkeratome device is to cut a portion of the cornea without completely severing it, abutting or stop means 65 are provided, which serve the purpose of limiting and preferably, completely stopping the movement of the cutting head assembly 50 from cutting completely across the cornea, that is, before the assembly has passed completely over the cornea. The abutting means or stop assembly are preferably disposed on the main housing 51. These features will be discussed in more detail below.

Still referring to FIG. 2, the preferred microkeratome device is also seen to include a coupling member 90. Coupling member 90 is structured and disposed to movably couple the cutting head assembly 50 to the positioning ring 32 while simultaneously permitting movement of the cutting head assembly 50 relative to positioning ring 32. As illustrated in FIG. 2, coupling member 90 comprises two segments: a) a retaining segment 92 and b) a pivot segment 95. The retaining segment 92 is structured and disposed to be fitted onto a top wall surface 56' of main housing 51 and may include downwardly depending flanges 91, 93 to snugly receive and grip a portion of housing 51 therebetween. The retaining segment 92 also includes an aperture 94 formed therein to correspond to aperture 58 of housing 51. As such, aperture 94 is sized and configured to allow passage of the driving shaft of the driving means 80 (shown in FIGS. 4 and 9) therethrough and into aperture 58 of the housing 51. Thus, in assembled form, coupling member 90 is securely yet removably coupled to head assembly 50 as a result of the engagement of the driving assembly 80 with the housing 51 through retaining segment 92. Turning to the pivot segment 95 of coupling member 90, it is structured and disposed to be coupled to rigid upstanding member 44 of positioning ring 32 and to permit coupling member 90, and accordingly, the cutting head assembly 50 connected thereto, to pivotally move about post member 45. Preferably, pivot segment 95 includes a bushing 97 having a bore 96 formed therein, which is sized to receive a substantial height of post member 45, thereby captivating it therein. Further, the pivot segment 95 preferably includes maintaining means 46, see FIG. 3, for maintaining rigid upstanding member 44 within bushing 97 and engagement means 98 for maintaining bushing 97 over rigid upstanding member 44. As illustrated in FIGS. 2 and 3, the maintaining means 46 preferably include an enlarged head 47 on rigid upstanding member 44, and an annular recess 48 or taper about the neck section of upstanding member 44. As illustrated, the engagement means 98 preferably comprise a threaded shaft which passes through a sidewall of bushing 97 and can be selectively moved into engagement with upstanding member 44 by rotating handle 99 and causing a tip thereof to extend into the annular recess 48, thereby preventing removal of the pivot segment 95 from the upstanding member 44, when surgery is to take place. It will be therefore be appreciated that in assembled form, the engagement means 98 and maintaining means 46 cooperate to permit coupling member 90 and cutting head assembly 50 to rotate about upstanding member 44 while preventing bushing 97 from sliding up and off of upstanding member 44. It will also be appreciated that in assembled form, upstanding member 44 acts as guide assembly for enabling the cutting head assembly 50 to be driven along an arcuate path in a smooth and controlled manner across positioning ring 32 and thus, the cornea C.

With reference to FIG. 2, the cutting head assembly 50 of the preferred microkeratome device as well as its operation will now be described in more detail. As previously recited, the cutting head assembly 50 comprises the main housing 51 which includes a top surface 561, a bottom wall, and a surrounding sidewall structure 53 defining a front end face 52, and an oppositely disposed rear end face 54. Because during surgery, the cutting head assembly 50 is driven across positioning ring 32 along an arcuate path, front end face 52 preferably defines a tapered nose to cooperate with the arcuate path of channel member 42. Also as previously recited, the main housing is structured to contain the cutting element 70, such as a cutting blade, and to operatively expose a cutting surface thereof. In order to accomplish this, the main housing 51 is preferably structured to define an interior chamber 88, therein, see FIG. 5, which is structured to receive in a cutting position and to accommodate the operation of the cutting element 70 during surgery, and preferably, of a blade cutting assembly 300, described more fully below. A cutting opening 56 is formed at a bottom of housing 51 so as to expose a cutting surface of cutting element 70, as is best illustrated in FIG. 5.

Additionally, in order to permit a used cutting element 70 to be removed and replaced, housing 51 includes access means 55. In one embodiment, and as seen in FIG. 5, access means 55 at least partially form bottom wall of housing 51 near rear end face 54, and ideally, comprise a door member 57 which is hingedly connected to the surrounding sidewall structure 53 at rear end face 54. Door member 57 is movable between a closed operative position for surgery and an open position for permitting a used or contaminated cutting element 70 to be removed from the housing 51 and replaced with a new or sterile cutting element. Door member 57 may be selectively maintained in the closed position by conventionally known fasteners as depicted in FIG. 5. It should be noted that the door member 57 does not completely bridge the cutting element 70, which is thought to offer a sturdier and less fragile structure so as to avoid bending the cutting element when it is inserted and closed into position for use within the microkeratome.

Figure 5:
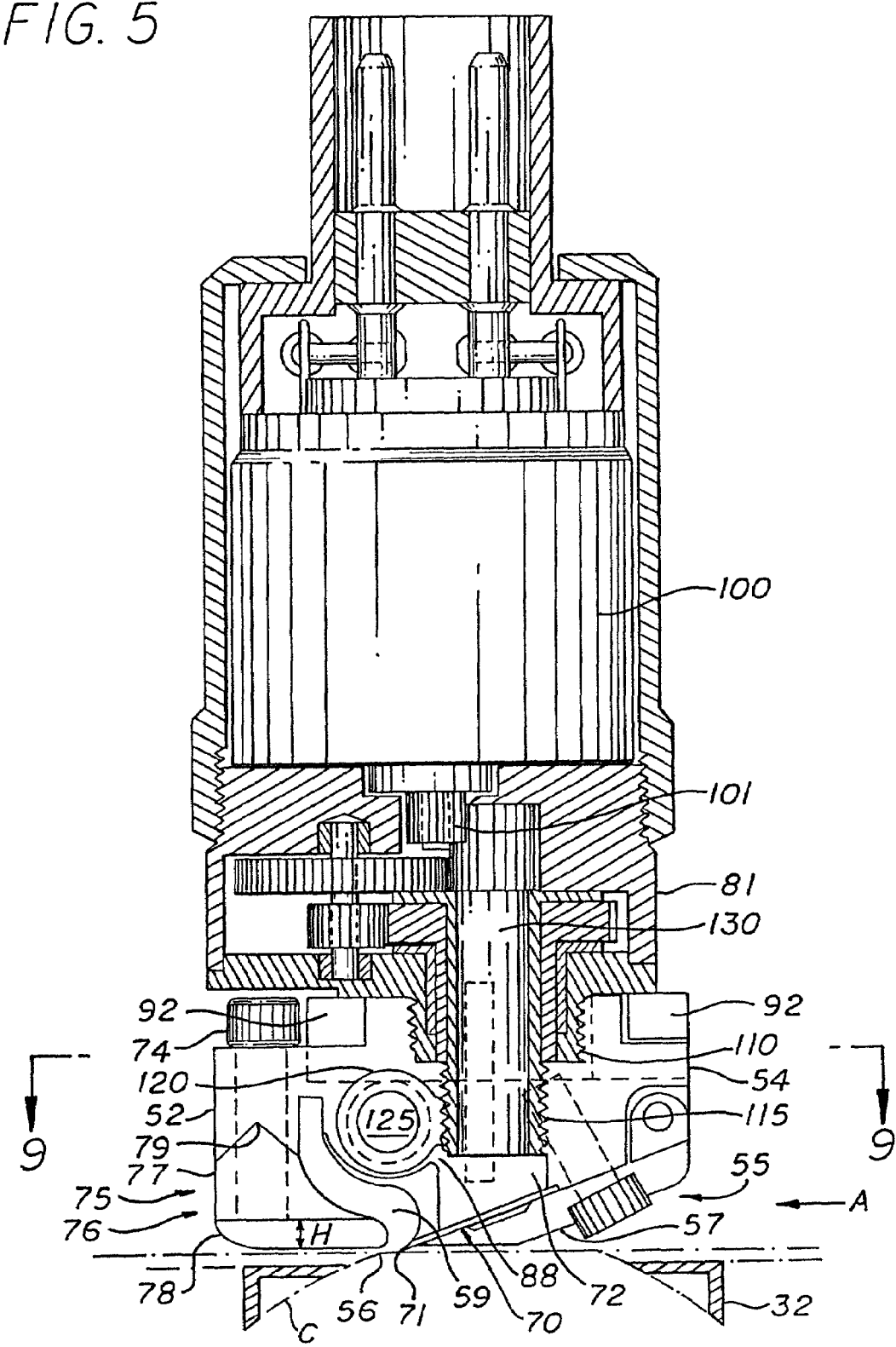
FIG. 5 is a partial cross sectional view of the preferred microkeratome illustrated in FIG. 4.

A unique feature of the present invention, however, is to provide the cutting head assembly 50 of the microkeratome device with improved access means, see FIG. 5-A, indicated generally by reference numeral 155, such that in preparation for surgery, a fresh and sterilized cutting element can be easily and quickly inserted within the cutting head assembly 50, with minimal handling so as to maintain it in a sanitary condition. Preferably, the improved access means 155 permit a fresh cutting element 70, and ideally, a cutting blade assembly 300 which includes both a cutting blade and a blade holder, described below, to be slidably inserted into the cutting head assembly, 50 and to be easily and yet properly secured in place therein in order for surgery to take place. To accomplish this, the improved access means 155 preferably comprise a side entry, access opening formed in the cutting head assembly 50. As illustrated in FIG. 5-A, more preferably, the surrounding sidewall structure 53 of the cutting head assembly 50 is structured to include an access opening 156 formed therein which further, is disposed to generally correspond and align with the location of interior chamber 88 of the cutting head assembly 50, so that the cutting element 70 may be received in a proper cutting position within the cutting head assembly 50 for surgery to take place. Ideally, the access opening 156 is structured and disposed to extend completely through the cutting head assembly 50 from one side of the surrounding sidewall structure 53 to the other, so that the cutting element 70 can be easily inserted from either side of the cutting head assembly 50. It should be appreciated from the foregoing that the improved access means 155 are additionally structured and disposed to permit easy and quick removal of a used and contaminated cutting element 70 from the cutting head assembly. It should further be appreciated that while the door member 57 of the cutting head assembly 50 can also be moved to an open position so as to permit insertion of a cutting element 70 within the cutting head assembly 50, the door member is preferably only moved to the open position to permit cleaning of other internal mechanisms disposed within the cutting head, whenever needed.

With reference to FIG. 5, the cutting element 70 will now be discussed. First, in the preferred embodiment, the cutting element 70 is disposed within the main housing 51 at about 20 to 30 degrees from the horizontal plane. Further, the cutting element 70 preferably includes a blade having a sharpened cutting edge 71, the cutting tip of which is preferably formed to have an angle of approximately and generally between 5 to 10 degrees from the horizontal axis of the blade. To accomplish these preferred goals, in a preferred embodiment, the cutting element 70 comprises a cutting blade operably connected to a blade holder 72. The blade holder is in turn, operably connected and disposed within the interior chamber 88 of the cutting head assembly 50 in communication with the drive assembly 80, see FIG. 9, which are in turn operably coupled to the housing 51 of the cutting head assembly 50, and microkeratome generally. As has been described, the drive assembly 80 imparts an oscillating movement to the blade holder 72, thereby causing the blade holder 72 and blade 71 connected thereto, to move back and forth within the interior chamber 88 of the cutting head assembly 50 and generally between opposite walls of the surrounding sidewall structure 53 thereof. Accordingly, the interior chamber 88 within housing 51 will be sized to receive both the cutting element, such as a cutting blade 70 and blade holder 72, and to permit the oscillating cutting movement of same within housing 51. So as to offer an improved microkeratome and cutting blade assembly that is able to cut and raise a microscopically thin layer of corneal tissue in a manner that results in very fine, smooth and almost undetectable cut corneal tissue edges, in a preferred embodiment, the drive assembly 80 will at least cause the blade holder 72 and blade 71 to oscillate at a very rapid rate, higher than that accomplished by other devices, such as generally about 5,000 to 10,000 times per minute, and ideally about 8,500 times per minute so as to offer an optimal corneal cut. Further in this regard, and as explained further below, the drive assembly may also preferably drive the cutting head assembly 50 across the positioning ring 30 and eye held therein, at a speed which takes the cutting head assembly 50 generally between 3 to 6 seconds, and ideally about 4 or 5 seconds. These preferred ranges for the cutting speeds of the microkeratome are thought to offer optimal and markedly improved cutting of the corneal tissues.

In addition, in order to accomplish the desirable goal of easily and quickly installing the cutting element 70 within the cutting head assembly 50, without excessive handling so as to maintain sterilization, the present invention comprises a cutting blade assembly, illustrated in FIGS. 6–8 and generally indicated by reference numeral 300. The cutting blade assembly 300 of the present invention is seen to comprise an improved cutting blade 310 and blade holder 320. The cutting blade 310 comprises a front portion 312 that includes a sharp, forward cutting edge 313, a rear, trailing portion 314 having a rear edge, 315, and a pair of side edges, 316, 317 that extend and taper between the front and rear trailing portions. In a preferred embodiment, the rear edge 315 is generally parallel to the forward cutting edge 313 of front portion 312. Also, the cutting blade 310 further includes at least one aperture, 318 formed therein, and preferably, a pair of apertures, 318 and 319 which are ideally circular in shape and disposed in the rear, trailing portion 314 in general alignment with one another. Preferably, the cutting blade 310 is substantially flat and made of stainless steel, with the front portion 312 of the cutting blade having an overall dimension which is larger than the rear trailing portion 314. In one embodiment, shown in FIG. 7, the side edges 316, 317 of the improved cutting blade 310' which extend between the front portion 312 and rear trailing portion 314, are rounded. This feature readily permits the operation of the cutting assembly 300 within the preferred microkeratome device that moves along an arcuate path over the position ring 32. More specifically, the cutting blade 310' shown in FIG. 7 is structured so that when it is oscillating during a surgery, wherein all or part of the blades' side edges might momentarily extend beyond the surrounding sidewall structure 53 of the cutting head assembly 50, it will not contact the positioning ring 32 nor otherwise interfere with the movement of the cutting head assembly 50 thereacross, along an arcuate path. The cutting blade 310, 310' can be formed to have other shapes to accomplish this same goal. For example, and as illustrated in FIGS. 6-A to 6-C, in a more preferred embodiment, the front portion 312 of the cutting blade 310 has a generally rectangular shape and the rear trailing portion 314 has a generally trapezoidal shape, such that the side edges 316, 317 thereof taper from a wider dimension of the front portion 312 to a smaller dimension in the rear trailing portion 314.

The cutting blade assembly 300 further comprises an improved blade holder 320. Blade holder 320 is formed so that an underside 321 thereof is secured to the cutting blade 310 at the at least one aperture 318 on the cutting blade, and so that a top side, 322, of the blade holder 320 includes means 325 for being operably driven by the drive assembly 80 of the microkeratome device. In the preferred embodiment, means 325 comprise a recess 326 formed within the blade holder, ideally having an oval shape, although the blade holder 320 could be formed to include a slot, groove or other shaped recess without departing from the scope of the present invention. Also in the preferred embodiment, the blade holder 320 will be molded of a plastic material and will be press fit during manufacture into the at least one aperture 118 on the cutting blade 310 so as to provide an integrally formed cutting blade assembly. It should be pointed out that by integrally forming the cutting blade 310 and blade holder 320, both parts which are contaminated during surgery, the cutting blade assembly 300 can be more readily removed from the cutting head 50 of the microkeratome, and further, if the blade holder 320 is formed of plastic, the cutting blade assembly 305 can be readily disposed of. Preferably, the blade holder 320 includes at least one lock segment 328 on its undersurface 321, which is structured and disposed to extend through the aperture 318 formed in the cutting blade 310 so as to become secured thereto. Most preferably, the blade holder includes a pair of lock segments formed to be circular in shape and which are structured to be snugly received within the preferred pair of apertures 318, 319 formed on the blade 310. Also in the preferred embodiment, the lock segment 328 includes a flanged portion 329 which is structured to engage at least partially about an edge of the aperture formed within the blade 310.

Referring now to FIG. 8, in a most preferred embodiment, the cutting blade assembly 300 of the present invention is seen to additionally comprise a tool 330 which facilitates the removal of the cutting blade 310 and blade holder 320 from a sterile packing container and the insertion thereof in a microkeratome device, while maintaining sterility. Preferably this tool is in the form of a handle assembly 360 connected to the blade holder 320 and structured to facilitate the introduction of the cutting blade assembly 300 into the access opening 156 of the cutting head assembly 50. In the preferred embodiment, the handle assembly 360 includes an elongate stem 362 structured to be threadingly coupled to the blade holder, ideally along a side wall thereof, so as to facilitate the introduction and installation of the cutting blade assembly 300 to and within the cutting head assembly 50. If desired, in this embodiment or in other embodiments, the handle assembly can be structured to permit the elongate stem 362 to be reconnected with the blade holder so as to remove a contaminated cutting blade assembly from the cutting head assembly 50, following a surgery. In an alternative preferred embodiment, the handle assembly 360 may include an elongate stem integrally formed with the blade holder and structured to be separated therefrom upon introduction and installation of the cutting blade assembly within the cutting head assembly 50. It should be appreciated that in this alternative preferred embodiment, the handle assembly may be comprised of a suitable plastic material so that it can be integrally formed with the preferred blade holder 320, and the entire cutting blade assembly can then be readily packaged in containers that permit sterilization prior to shipping, and which remain sterilized during shipping. In this way, the handle assembly 360 with the cutting blade assembly 300 connected thereto, can be easily removed from the sterile packaging and the handle assembly 360 used to quickly and easily insert the cutting blade assembly 300, while maintaining it in a sanitary condition, into the microkeratome's cutting head assembly, 50. Thereupon, the handle assembly 360 can be broken off from the cutting blade assembly 300 and discarded or otherwise disposed of.

Referring back now to FIG. 5, other features of the preferred microkeratome device will be described. In the preferred embodiment, the housing 51 of cutting head assembly 50 will include depth adjusting means 75 for adjusting the depth at which cutting element 70 cuts into the cornea. As illustrated in FIG. 5, the depth adjusting means 75 are preferably disposed at the front end face 52 of main housing 51 and form at least a portion of the bottom wall of housing 51 near front end face 52. Preferably, the depth adjusting means 75 comprise a separate nose segment 76, which is structured to be securely, yet removably interconnected with housing 51 by way of a conventionally known fasteners 74 such as a screw, a bolt, etc. Preferably, the nose segment 76 comprises an engagement segment 77 and a variable depth plate member 78. Engagement segment 77 preferably includes a terminal end 79 which is formed to define an inverted "V" shape, and preferably extends across the width of the nose segment 76. This structure is sized and configured to be received and to nest within a corresponding void, also shaped like an inverted "V", formed within housing 51 on and between oppositely disposed sidewall structures 53, adjacent front end face 52. It will be appreciated that this structure permits a highly stable nesting or dwelling of terminal end 79 within housing 51 even as the cutting head assembly 50 is moved along an arcuate path over positioning ring 32. Further, as illustrated, variable depth plate member 78 is preferably integral with engagement segment 77 and is disposed substantially in the horizontal plane. Variable depth plate member 78, has a depth depicted as "H" in FIG. 5, which is a dimension pre-selected by the surgeon to correspond the desired depth of the cut to be made into the cornea. Another feature of the present invention is to provide a plurality of nose segments 76, each including a plate member 78 having a differently dimensioned depth "H". It will be appreciated from FIG. 5 that there is an inverse relationship between the depth of plate member 78 and the depth of the cut to the cornea as the cutting head assembly 50 proceeds forward during surgery in the direction of the arrow "A" and pushes down on the cornea. For example, a plate member 78 having a larger depth "H" will shield more of the blade's cutting edge 71 whereas a plate member 78 having a smaller depth "H" will expose more of area above the blade's cutting edge. It will thus be recognized that the cutting head assembly 50 is designed to be interchangeable with differently sized depth adjusting means 75 so as to precisely meet the needs of the patient undergoing surgery. Ideally, the present invention will offer two differently sized nose segments 76, namely one sized for 130 microns and another for 160 microns which are currently the most desirable depths for cutting into the cornea and exposing same for reshaping.

As has been described, housing 51 of cutting head assembly 50 also includes tracking means 60. Referring to FIG. 2, tracking means 60, which in the preferred embodiment are disposed on a lower peripheral zone of housing 51, are structured for mating communication with and tracking within channel member 42, see FIG. 3, of positioning ring 32. For example, in the preferred embodiment the tracking means 60 are disposed on the depth adjusting means 75 and are integral with and planar to the variable depth plate member 78 in the form of a flange 62, see FIG. 2. Preferably, flange 62 extends out beyond the periphery defined by surrounding sidewall 53 of housing 51 in generally perpendicular relation thereto. Further, although the cutting head assembly 50 is designed to receive nose segments 76 having variable depth plate members 78, flange 62 which extends therefrom is of a uniform height so as to correspond and effect mating communication with and tracking within channel member 42, of positioning ring 32. Although flange 62 could extend only from one side of the housing 51, in the preferred embodiment, flange 62 is disposed on each side of variable depth plate member 78, thereby facilitating use of the present invention on either a patient's left or right eye.

Also as previously recited, the main housing 51 includes abutting or stop means 65 which serve the purpose of limiting and preferably stopping, the forward movement of cutting head assembly 50 across positioning ring 32. In the preferred embodiment, stop means 65 are formed generally at rear end face 54 on surrounding sidewall structure 53 and are seen to comprise a shoulder 66 formed at the juncture between sidewall structure 53 and rear end face 54 of the housing 51, which shoulder is sized to be too large to pass within the channel member 42 of the guide means 40, thereby preventing any further forward motion of the head assembly 50 across positioning ring 32. When abutting engagement occurs between shoulder 66 and channel member 42, by way of lip 43', the driving means 80 can be stopped and then reversed to permit movement of the cutting head assembly 50 in the opposite direction. As has been described, it has been determined in recent years that in performing surgery on the cornea, the layers of the cornea which are cut should not be completely severed. A unique feature of the cutting head assembly 50 and of this invention 10 is that the cutting of the cornea, C, results in the formation of a corneal flap F, as illustrated in FIG. 1, which is also safely preserved by the assembly 50. To preserve the corneal flap F, housing 51 includes a flap receiving gap 59 formed within housing 51. As illustrated in FIG. 2 and more clearly in FIG. 5, flap receiving gap 59 is disposed generally near the front end face 52 of housing 51 and more particularly, is defined by a gap formed just forward of the blade's cutting edge 71 and just rearward of variable depth plate member 78. Thus, flap receiving gap 59 is disposed on an undersurface of housing 51 and extends upwardly and into housing 51. Ideally, flap receiving gap 59 extends through the opposite sidewall structure 53 of housing 51.

In preparation for cutting the cornea with the preferred microkeratome device: a) a sterilized improved cutting blade assembly 300 is slidably moved into position within the cutting head assembly 50, and b) the coupling member 90 is mounted on the cutting head assembly 50 and the drive means 80 connected to and engaged therewith. Referring to FIG. 2, as an additional feature, the cutting head assembly 50 may include indicia 67 for indicating to a surgeon which eye the device is in position to cut. For example, it is preferred that indicia such as the letter "L" as an abbreviation for "Left" or "left eye" and the letter "R" as an abbreviation for "Right" or "right eye" be utilized, or their equivalents in words or abbreviations in a foreign language or symbols. This indicia will preferably appear on opposite sides of the surrounding side wall structure 53 of the main housing 51 of the cutting head assembly 50, in a location which will be selectively concealed by the coupling member 90. In particular, when operably coupled with the cutting head assembly 50 and disposed over so as to cut the right eye, the coupling member 90 extends down the left side of the main housing 51 of the cutting head assembly 50, leaving only the right side, and preferred "R" indicia positioned thereon, visible. Conversely, when assembled to cut the left eye, the coupling member 90 extends down the right side of the housing 51, leaving only the left side and the indicia positioned thereon readily visible. As such, it is seen that a further safety feature directed towards ensuring proper alignment of the device on a patient's eye is achieved.

To continue, once the positioning ring 32 has been centrated on the eye with a proper vacuum applied to temporarily attach it thereto, c) the tracking means 60 of the head assembly 50 can be matingly connected to the guide means 40 of positioning ring 32 in an initial or start position. Once power is supplied to the microkeratome device, the cutting head assembly 50 may move across the positioning ring 32 with cutting of the cornea C, taking place until the stop means 65 contact channel member 42 of the positioning ring 32, to limit and preferably, prevent any further forward motion of the assembly. It should also be clear that in this stopped position, the cutting element 70 has not moved completely across the cornea C, but rather has cut a portion of the cornea up until this point, creating a corneal flap which is left attached to the cornea as designated by the area marked "F" which is shown in the FIGS. 10-A and 10-B. Moreover, as illustrated in FIG. 5, the corneal flap created has been directed by the forward movement of the assembly, upwardly and into flap receiving gap 59 of housing 51 to be preserved and kept clear of cutting element 70. Once the assembly has been stopped as in FIG. 10-B, the drive means 80 can be reversed to permit movement of the cutting head assembly 50 in the opposite direction, which does not result in any further cutting of the cornea, but rather, in the safe removal of the corneal flap F out of flap receiving gap 59 of housing 51. Thus, when the cutting head assembly 50 returns through to a position analogous to that shown in FIG. 10-A, it can be disengaged from the retaining means 30. The corneal flap F can then be maneuvered so as to permit the cornea to be reshaped, preferably by way of a laser surgical procedure. Once the surgery has been completed, the corneal flap is returned to a covering relation over cornea.

Another unique feature of the present invention is not only that a corneal flap can be created, but significantly, that the corneal flap is positioned in such a way that the blinking of the eye will not improperly position the corneal flap on the cornea following surgery. Referring again to FIGS. 10-A and 10-B, the preferred microkeratome device is schematically illustrated on both a patient's left and right eyes. As depicted in FIG. 10-A, reference points of the work environment can be equated with the position of some numerals on the face of a clock. Thus, in FIG. 10-A, it will be noted that with respect to the patient's left eye, the cutting head assembly 50 in the initial position is preferably disposed at a generally five o'clock position with respect to the patient's right eye, the cutting head assembly 50 in the initial position is preferably disposed at a generally seven o'clock position. Turning now to FIG. 10-B, the cutting head assembly 50 is shown to have moved towards a position generally aligned with the twelve o'clock position, wherein the stop means 65 are in abutting engagement with channel member 42 of the positioning ring 32, such that any further forward motion of the assembly is prevented. It will thus be appreciated that regardless of whether the surgical procedure is being performed on a patient's left or right eye, the cutting head assembly 50 is preferably aligned generally with a twelve o'clock position. It will also be appreciated from FIG. 10-B that the resulting corneal flap F, remains attached to the cornea at an upper region thereof. As a result, following the surgical procedure to reshape the cornea, the orientation of the corneal flap will be in generally the same direction as the natural blinking action. That is, it is believed that the downward blinking motion of the patient will tend to stroke the corneal flap down and thereby assist with maintaining the corneal flap in proper re-position on the cornea so as to avoid the development of astigmatism.

Figure 9:
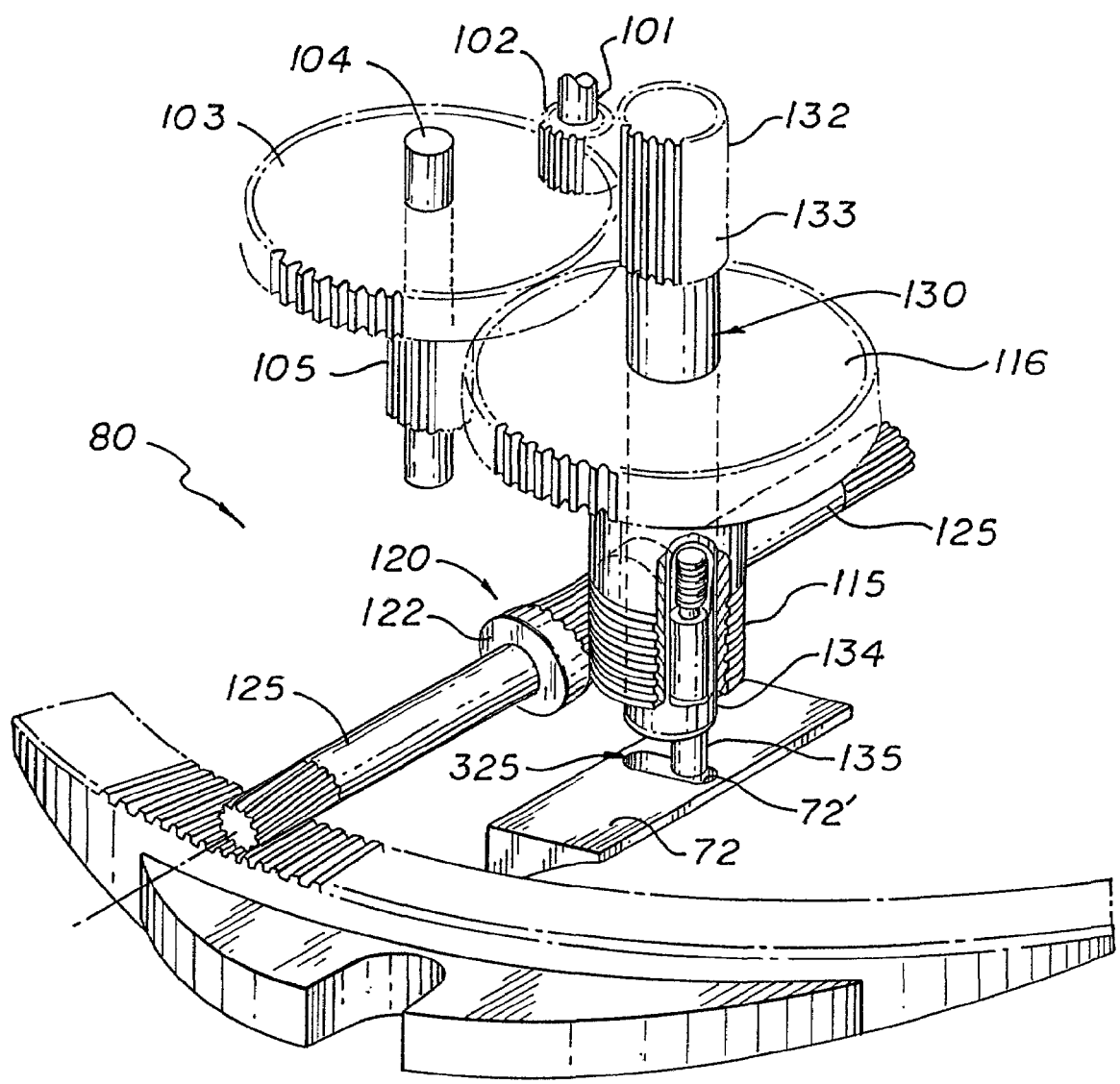
FIG. 9 is an isolated perspective view of the drive means for the preferred microkeratome device and illustrating the operation and interconnection of the worm, worm gear, and oscillating shaft with the means of the blade holder, in the form of a recess, for being operably driven by the drive means of the microkeratome device.

Referring now to FIG. 9, the present invention includes a drive assembly 80 both: a) for driving the cutting head assembly 50 across the previously described eyeball retaining and positioning means 30; and/or b) for causing the cutting element 70 to oscillate back and forth within housing 51. The drive assembly 80 in a most preferred embodiment will drive the cutting head assembly 50 across the eyeball retaining and positioning means 30 and eye held therein, at a speed which takes the cutting head assembly generally between 3 to 6 seconds in the first direction, and similarly in the opposite direction. Also, in a preferred embodiment, the drive assembly 80 include among other items, discussed below, a motor 100, which is electrically operated and more preferably, a micromotor capable of operating at a constant and uniform speed, regardless of the load. Specifically, under normal circumstances the natural resistance encountered by the cutting head assembly 50, as it is driven over the cornea, would result in an increased torque load upon the micromotor, which would tend to cause a voltage drop in the internal resistance of the motor 100 and therefore a drop in speed. While some known systems for microkeratome devices attempt to avoid excessive drops in speed by incorporating an overpowered motor to keep losses below a 10% slow down, the motor 100 of the present invention is preferably equipped to monitor current flowing therethrough, such as by using an op amp, and to utilize that information to control the applied voltage and maintain a generally constant speed. This monitoring and compensation, sometimes referred to as I R compensation, thereby permits a conventional 12 V supply module, dropped through said compensation, to be used with a DC motor of lower nominal voltage, in order to maintain the effective constant speed of travel of the cutting head assembly 50 over the eye.

Figure 4:
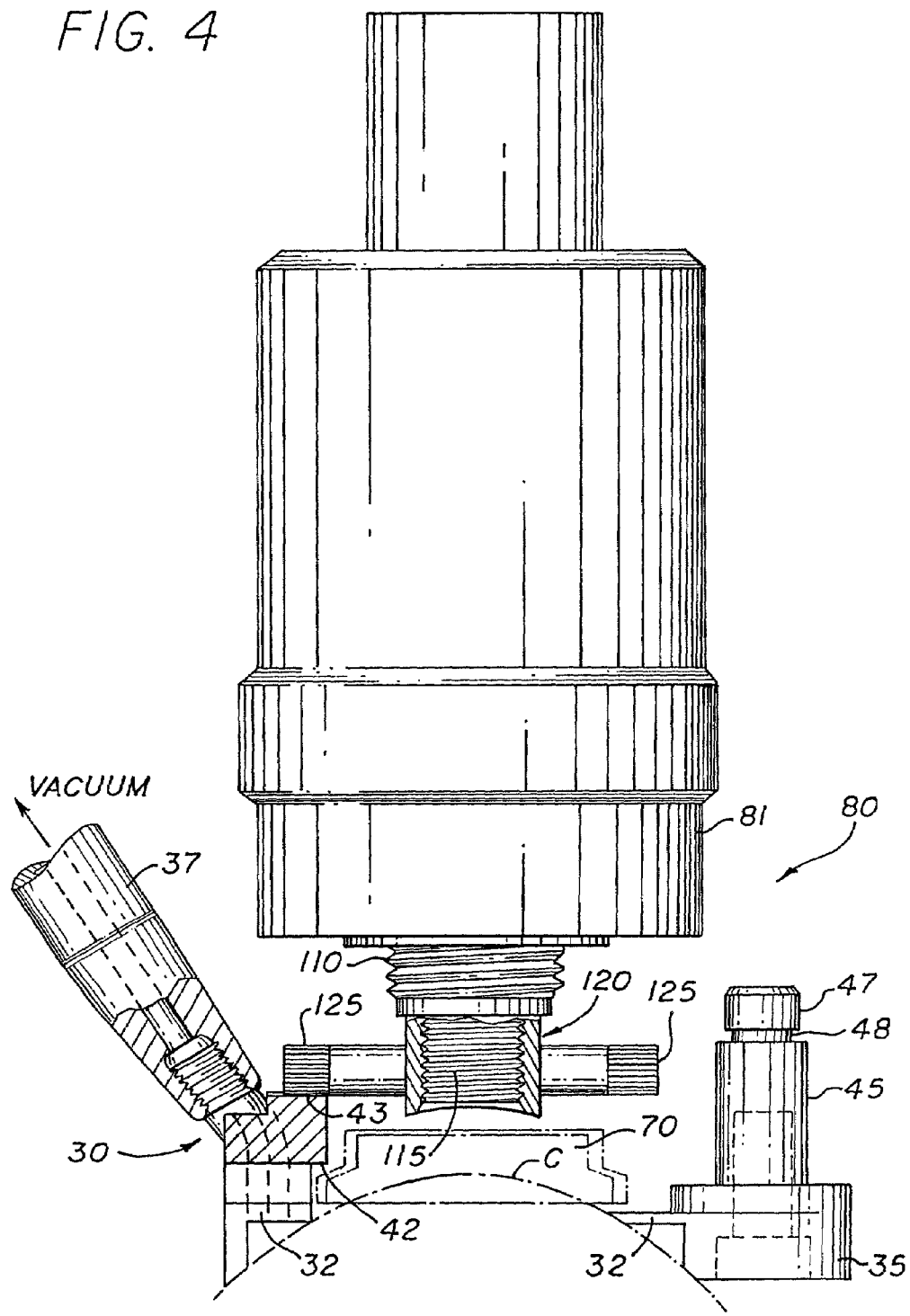
FIG. 4 is a partial side view of the preferred microkeratome illustrated in FIG. 2 in assembled form and in position on a patient's cornea.

Referring now to FIG. 4 and again to FIG. 9, the drive assembly 80 of the microkeratome device is seen in the preferred embodiment to further include a gear box 81 into which a motor main drive shaft 101 extends. From the gear box 81, and specifically concentrically through an engagement hub 110 as shown in FIGS. 4 and 5, a cutting assembly main drive shaft operatively extends. The cutting assembly main drive shaft comprises two primary sections, namely: a) a threaded drive screw or "worm" 115 shown in FIG. 9, which is an intermediate section that extends through the engagement hub 110; and b) an oscillation shaft 130, also shown in FIG. 9, and which is the inner most section and extends through the worm 115.

Turning first to the engagement hub 110, shown in FIG. 4, it is an outer most section that preferably extends downwardly from the gear box 81 and is structured to be matingly, and preferably threadingly engaged within the threaded aperture 58 formed in the main housing 51. As such, the engagement hub 110 functions to secure the drive assembly 80 to the cutting head assembly 50. Further, it will be recognized that the drive assembly 80 is thereby permitted to enter the cutting head assembly 50 through a top surface 56' and is thus, generally vertically disposed. It is believed that this feature results in less interference with the surgical field and facilitates finer handling by the surgeon than is offered by conventionally known microkeratomes. Specifically, known microkeratomes have typically provided for horizontally disposed drive means, which resulted in the surgeon having to handle a cord of the driving means, which if not held properly could cause drag on the operation of the microkeratome and/or result in a different pressure being applied to the microkeratome. Moreover, the structure of the present invention maintains its center of gravity substantially over the center of the eye, unlike old systems, thereby providing increased balance and ensuring that the cutting head assembly does not inadvertently tip away from the surface of the eye during use.

As illustrated in FIG. 5, the oscillation shaft also extends from the gear box 81. Turning now to FIG. 9, the oscillation shaft 130, which extends into the housing 51 through its aperture 58, is preferably an independent element that extends concentrically through and protrudes from both ends of the worm 115. The oscillation shaft 130, which is preferably structured to freely rotate relative to the worm 115 includes an upper drive portion 132 which may be welded onto shaft 130 but which is in any event, drivingly engaged with a main drive gear 102 secured to the motor main drive shaft 101. Accordingly, rotation of the motor main drive shaft 101 results in corresponding rotation of the oscillation shaft 130. Further, protruding off center from an opposite end 134 of the oscillation shaft 130 is an oscillation pin 135. The oscillation pin 135, which is preferably downwardly biased to maintain engagement pressure on the cutting element 70 is structured to extend into a slot 72' formed in an upper surface of the preferred blade holder 72 or other means 325 formed on the blade holder for receiving the oscillating pin and permitting it to impart movement thereto. As such, upon axial rotation of the oscillation shaft 130, the oscillation pin 135 rotates a predetermined radius off center and alternatively engages opposite side edges of the slot 72' of the blade holder 72 to result in alternating, oscillating movement of the blade holder 72 and the cutting blade held thereby.

Still referring to FIG. 9, the oscillating shaft 130 further includes a secondary drive portion 133. The secondary drive portion 133 is drivingly connected with a first interior drive gear 103 contained within the gear box 81. The first interior drive gear 103 is connected with and is drivingly secured to an interior drive shaft 104, which preferably includes a second interior drive gear 105 disposed thereon in spaced apart relation from the first interior drive gear 103. As such, upon rotation of the oscillation shaft 130, the second interior drive gear 105 also rotates.

Again with reference to FIG. 9, drivingly connected with the second interior drive gear 105 and structured to extend from an interior of the gear box 81, concentrically through the engagement hub 110, is the threaded drive screw or "worm" 115. The worm 115, which extends up into the gear box 81 includes a drive head 116 which engages the second interior drive gear 105. As a result, upon rotation of the interior drive shaft 104, the worm 115 correspondingly rotates within the housing 51 of the cutting head assembly 50. Further, rotatably disposed within the housing 51, in operative engagement with the worm 115, is a worm gear 120. The worm gear 120 preferably includes an increase diameter central portion 122 having a plurality of drive recesses formed about a perimeter thereof and structured to engage the exterior threaded surface of the worm 115 such that the central portion 122, and accordingly the entire worm gear 120, rotates about a horizontal axis as a result of the rotation of the worm 115 about a vertical axis. It is noted that the screw-like threaded surface of the worm 115 enables the worm 115 to rotate without moving vertically and successively engage the drive recesses on the worm gear 120 to effect rotation thereof. Extending from at least one, but preferably both vertical faces of the central portion 122 of the worm gear 120 is a propulsion shaft 125. The propulsion shaft 125, which comprises additional tracking means, is structured to protrude from the sidewall structure 53 of the main housing 51 and engage the toothed track 43 on the positioning ring 32 such that upon rotation of the worm gear 120, and accordingly rotation of the propulsion shaft 125, the propulsion shaft 125 rides along the toothed track 43 and drives the cutting head assembly 50 across the positioning ring 32 smoothly and at a steady and defined pace. Furthermore, it is seen that by reversing the rotational direction of the interior drive shaft 101 within the gear box 81, the direction of rotation of the worm 115 and therefore the worm gear 120 are reversed to effectuate reverse driven movement of the cutting head assembly 50 over the positioning head 32. Also, so as to facilitate movement over toothed track 43 and the arcuate path thereof, it is preferred that the propulsion shaft 125 portion of the worm gear 120 include a helical gear configuration or plurality of angled ridges to permit more effective alignment with the curved toothed track 43 and movement thereover.

Considering the motor 100, once again, it is preferred that it be controlled by a foot pedal or like actuation means. In the case of a foot pedal, it is preferred that it be a dual function foot pedal such that one side will function to drive the motor main drive gear 101, and therefore the cutting head assembly 50 in a forward direction, and the second side will drive them in a reverse direction. Further, the system may be set to a manual mode whereby a doctor must affirmatively reverse the direction of movement, or an "auto-reverse" mode wherein upon the cutting head assembly 50 traveling its maximum distance it automatically reverses direction. In either case, however, the device will preferably be equipped with a sensor, such as a proximity sensor of any type or as in the preferred embodiment a sensor associated with the motor 100 and structured to detect an abrupt current increase such as that exhibited upon encountering a mechanical stop. Specifically, when the cutting head assembly 50 reaches the stop means 65 and further forward movement is either partially or completely resisted, an abrupt current increase will generally occur in the motor 100. That abrupt current increase, once detected, can signal either the power to shut off, or the reverse movement to commence, depending upon a doctor's desired setting.

As has been described, the preferred microkeratome device can be utilized on both eyes of the patient, see FIGS. 10-A and 10-B. Specifically, as worm gear 120 runs through housing 51 and juts out of the opposite surrounding sidewall structure 53 of housing 51, the cutting head assembly is ready to use on the opposite eye of a patient. In order to accomplish this, and due to the symmetric shape of the cutting head assembly 50, the drive means 80 need only be removed from the housing 51 and thus, coupling member 90, whereupon, it can be re-oriented 180 degrees for use with the opposite eye of a patient.

Considering the drive assembly 80 once again, it should be noted that it must generally operate in conjunction and in harmony with the suctioning assembly applied to the positioning ring 32 when surgery is performed on an eye. Accordingly, the present invention is further directed towards incorporating both the drive assembly 80 and the suctioning assembly as part of an overall control assembly 200. The control assembly 200 of the present invention includes a portable housing 205 from which power and control are supplied through a cable 203 to the portion of the drive assembly 80 which interacts with the cutting head assembly 50, and from which a vacuum source of the suctioning assembly is supplied through the vacuum hose 202. The suctioning assemblies and the vacuum source which it provides will be addressed first. Specifically, the vacuum source generally includes a vacuum pump 210 contained within the housing 205, which is powered from a conventional power supply, such as an internal or external power module and/or power source, and which operates to create the vacuum which results in a suction at the positioning ring. In addition to the vacuum pump 210, however, the suctioning assembly of the present invention further include a reserve vacuum tank 215. The reserve vacuum tank 215 is structured to be evacuated upon activating the control assembly 200 and maintained generally at an operational level. Moreover, in the event that the operation of the vacuum pump is interrupted, such as due to a power loss, the reserve vacuum tank 215 is preferably structured to maintain a sufficient vacuum to continue the positioning ring's hold on the eye until the movement of the cutting head assembly 50 over the eye is completed. Specifically, the control assembly 200 is structured such that the reserve vacuum tank 215 is preferably continually operational and such that in the event of a power loss or other interruption to the operation of the vacuum pump 210, a check valve isolates the vacuum pump 210, the necessary vacuum is maintained by the reserve vacuum tank 215, and a complete cutting pass across the eye is not dangerously and unexpectedly interrupted due to an interruption in the operation of the vacuum pump 210.

According to the present invention, the vacuum pump 210 is preferably controlled by a computerized processor control 220 within the housing 205. The processor control 220 performs a number of functions at all times including when the control assembly 200 is turned on and/or is in a "Ready" mode. In particular, when the control assembly 200 is first turned on, it is structured to conduct a number of internal tests, as indicated on a display screen 211, and the vacuum pump 210 is preferably directed to first generate a vacuum in the reserve vacuum tank 215. Next, the vacuum pump 210 will preferably continue to run until a desired vacuum relative to atmospheric pressure is generated. Once the desired vacuum is achieved, however, operation of the vacuum pump is cycled. For example, once a desired level is attained, the vacuum pump 210 is turned off until the vacuum drops below a certain point relative to atmospheric pressure. At that point, the vacuum pump 210 is preferably turned on once again by the processor control 220 in order to raise the vacuum back up above the desired level. In this manner, an operable back-up vacuum is available, if ever it should be needed.

In the preferred embodiment, the control assembly 200 remains in the "Ready" mode until a user wishes to begin an operation or to conduct further testing, if that is desired. When, however, it is time to begin an operation, a user typically presses a foot pedal 216 or other switch to activate the vacuum and shift the control assembly into an "Operating" mode. Before entering the "Operating" mode, a "Pre-op" mode is preferably initiated wherein the control assembly 200 completes a number of internal tests. Unlike the "Ready" mode, once in the "Operating" mode, the vacuum pump 210 will preferably remain on, thereby ensuring that a sufficient vacuum will always be present. Furthermore, so as to ensure that a malfunction in the processor control 220 does not interrupt the cutting process, once the "Operating" mode is entered, control of the motor 100, to be described in greater detail subsequently, is preferably removed/interrupted from the processor control 220, such that the processor control 220 only acts in an advisory capacity as to the performance of the motor 100 and mechanism, providing warning messages and data, and is transferred to an independent logic control 225, such as one embodied in one or more PAL chips. Preferably, this transfer of control is achieved utilizing at least one latching switch 228 connected between the processor control 220 and the independent logic control 225. The latching switch 228 is normally positioned so that the processor control 220 at least partially directs the operation of the motor 100, however, when the "Operation" mode is entered, it is switched so as to eliminate dependency on the processor control 220, so that the back up power source 260 becomes operational, and so that the independent logic control 220 directs the operation of the motor 100 without processor influence. Preferably, this "Operation" mode orientation of the latching switch 228 is maintained until affirmatively reset by a user. For example, pressing foot pedal 216 once again will reset control to its "Ready" mode state.

Still addressing the suctioning assembly, although the powering of the vacuum pump 210 may require a high voltage, it, as well as all other high voltage aspects of the control assembly 200, must be isolated from a low voltage portion of the circuitry which comes into contact with the patient. In this regard, in some instances a momentary removal of power to the vacuum pump 215 can sometimes occur, thereby requiring a resetting of certain conditions before the pump can restart and normal running can proceed. For example, in the preferred embodiment, if while in the "Operate" mode the current drawn by the vacuum pump 215 momentarily jumps from approximately 0.6 amps to approximately 1.3 amps, the control assembly 200 will generally identify a pump restart. If the pump fails to restart, the vacuum reserve tank operates to maintain the vacuum so as to enable a surgery in progress to be completed. Normally, however, the pump is able to restart, and normal running of the vacuum pump resumes. However, even if the vacuum pump is able to restart, the vacuum pump will typically not resume operation if a full vacuum is still present, thereby requiring a momentary release of vacuum prior to achieving the restart. The release of vacuum, however, is triggered from controls on the low voltage side of the control assembly 200. Therefore, the present invention preferably utilizes an optic switching assembly 240 to trigger the momentary release of vacuum with the required electrical isolation. In particular, when the previously described typical current jump associated with a pump restart is exhibited, that current jump typically gives rise to an instantaneous voltage increase from a normal peak of less than 0.9v to a normal peak of at least 1.25v across a preferably 0.75 ohm resistor 241, and is sufficient to illuminate an LED 242 of an optic coupler 240'. The LED 242 illuminates a light actuated semi conductor 243 of the optic coupler 240' via a galvanically isolated path. Preferably through a pulse extender, a semiconductor chip 245 is then actuated and in turn actuates a valve 247 to cause the momentary release in vacuum required for the restart and continuing operation of the vacuum pump 210. Accordingly, complete isolation is maintained between the high voltage and low voltage sides of the assembly. Indeed, this process is also utilized during the described pump cycling in the "Ready" mode.

Turning now to the other aspect affected by the control assembly 200, namely, the drive assembly 80, it is preferably powered by a motor 100, such as low power DC, pneumatic or hydraulic motor. The motor 100 is sufficient to drive the cutting head assembly 50 across a positioning ring, such as 32, and will preferably operate in both a forward and a reverse direction. Furthermore, during normal forward operation, the control assembly 200 is structured to detect an increase in amperage above a certain predetermined limit, typically a 300 milliamp level, which is a typical indication that movement of the cutting head assembly 50 has been blocked and that the activity of the motor 100 and drive assembly is being resisted. A stop of the cutting head assembly 50 can occur either due to the presence of an obstacle on the cutting path over the positioning ring, such as a number of eyelashes or other debris, or due to the normal stopping of the cutting head assembly 50 because it has made a complete cut reaching the mechanical stop means. In any event, however, if the motor 100 pulls to the 300 milliamp level after a normal 3 second run, the motor 100 shuts off and is dynamically braked until restarted by the user. To restart, in preferably only an emergency situation, the user may temporarily remove pressure from the foot pedal 252 so as to restart and then again activate the foot pedal to result in a continued movement of the motor 100 for another three (3) seconds, during which the only limitation upon the power to the motor 100 is a defined current limit of preferably approximately 400 milliamps. Indeed, this more absolute limit of 400 milliamps is in effect at all times, including during motion in both the forward and reverse directions.

In addition to stopping the operation of the drive assembly 80 because of a movement stoppage, in the event of a loss of suction at the positioning ring, which may result in temporary or complete detachment of the positioning ring from the eye, the control assembly 200 is preferably further structured to immediately shut off and dynamically brake the motor 100, and therefore, the drive assembly. As a result, the cutting head assembly 50 will not continue to cut if there is even a momentary break in the suction of the positioning ring to the eye. Moreover, if such a shut down occurs, complete re-initiation of the operating mode, including the normal array of systems checks and the re-establishment of the vacuum, must preferably be achieved before operation of the motor 100 can resume. Still, re-initiation is never recommended until after a proper healing period has passed.

As indicated, the vacuum pump 210 of the present invention preferably includes a backup, in the form of the vacuum reserve tank 215, that maintains vacuum if the vacuum pump 210 fails, such as due to a power loss. Similarly, the motor 100 preferably includes a backup power source 260, such as one or more lithium batteries, disposed within the housing 205 of the control assembly 200. The backup power source 260 is most preferably included within and as part of the control assembly 200 and functions to immediately continue to supply operating power to the motor 100 in case of a power loss from a typical power supply, whether an internal module and/or external source. As such, a completed pass across the eye can be normally completed if a power failure occurs.

Lastly, it is noted that in some instances a user that is monitoring patient conditions may already be viewing a computer display console that monitors other patient conditions. As such, the control assembly 200 of the present invention includes a connection port 265, such as a serial connection port, through which a computer interface can be achieved and through which data relating to the operation of the control assembly 200 can be transmitted for convenient use and display on the computer display console. An electrically isolated, bi-directional computer port, such as an RS232 port with optically isolated data and transformer isolated power is preferred for communication with a host laser system or isolated computer system. For example, the laser systems typically employed in the corrective procedures generally include an elaborate computer control. This laser computer control directs the corrective procedure and monitors the status of the operation throughout. As such, by interfacing the control assembly 200 with the laser computer control, the actual operating conditions of the present invention can be equivalently monitored and recorded.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described.

What is claimed is:

1. A microkeratome cutting blade assembly for use with a surgical device that cuts at least partially across the cornea of an eye of a patient along an arcuate path, comprising:
    a blade having a blade holder attached thereto;
    said blade having a front portion and rear portion;
    said front blade portion having a cutting edge for cutting a portion of the cornea of an eye;
    said front portion having an overall dimension which is larger than the rear portion;
    said blade having an edge for engaging said blade holder;
    said blade holder having a top side and an underside said underside having a flanged portion which engages said edge whereby moving said blade holder correspondingly moves said blade; and
    an underside of said blade being inclined at an angle with respect to said top side, said top side adapted to be driven by a pin.

2. A microkeratome cutting blade assembly for use with a surgical device that cuts at least partially across the cornea of an eye of a patient along an arcuate path, comprising:
    a blade having a blade holder attached thereto;
    said blade having a front portion and rear portion;
    said front blade portion having a cutting edge for cutting a portion of the cornea of an eye;
    said front portion having an overall dimension which is larger than the rear portion;
    said blade having an edge for engaging said blade holder; and said blade holder having a top side and an underside, said underside having a flanged portion which engages said edge whereby moving said blade holder correspondingly moves said blade.

3. A microkeratome cutting blade assembly as recited in claim 2 wherein an underside of said blade is inclined at an angle with respect to said top side, said top side adapted to be driven by a pin.

4. A microkeratome cutting blade assembly as recited in claim 2 wherein said front blade portion has a front dimension and said read blade portion has a rear dimension, said front dimension being wider than said rear dimension.

5. A microkeratome cutting blade assembly as recited in claim 4 wherein said front dimension of said front blade portion is defined by said cutting edge, which is wider than any dimension of said rear blade portion.

6. A microkeratome cutting blade assembly as recited in claim 2 wherein said blade holder is formed from a plastic material and is attached to said blade by a press fit.

7. A microkeratome cutting blade assembly for use with a microkeratome that cuts at least partially across the cornea of an eye along an arcuate path, comprising:
    a blade having a blade holder attached thereto;
    said blade having a front portion and a rear portion;
    said front blade portion having a cutting edge for cutting a portion of the cornea of an eye;
    said rear portion including a side edge which is tapered with respect to said cutting edge;
    said blade holder having an underside secured to said blade and a top side including a recess adapted to receive an oscillation pin.

8. A microkeratome cutting blade assembly as recited in claim 7 wherein said recess is structured to receive said oscillation pin from a generally vertical plane.

9. A microkeratome cutting blade assembly as recited in claim 7 wherein said blade holder includes a sidewall which extends between said top side and said underside, said sidewall generally tapering from a front of said blade holder to a back of said blade holder.

10. A microkeratome cutting blade assembly as recited in claim 7 wherein said blade further comprises an edge and said blade holder comprises a flange for engaging said edge.

11. A microkeratome cutting blade assembly as recited in claim 7 wherein said tapered side edge comprises a generally linear taper.

12. A microkeratome cutting blade assembly as recited in claim 7 wherein said tapered side edge comprises a generally rounded taper.

13. A microkeratome blade assembly comprising: a blade holder and a cutting blade connected to said blade holder, wherein said blade holder includes a top side including means for being operably driven by an oscillating pin.

14. A microkeratome blade assembly as recited in claim 13 wherein said means for being operably driven comprise a recess.

15. A microkeratome blade assembly as recited in claim 13 wherein said blade is shaped so as to avoid interference with movement along an arcuate path when oscillated.

16. A microkeratome blade assembly as recited in claim 13 wherein said blade comprises a cutting edge, said cutting edge being wider than at least another portion of said blade.

17. A microkeratome blade assembly as recited in claim 13 wherein said blade further comprises at least four edges.

18. A microkeratome blade assembly as recited in claim 13 wherein said blade further comprises a front portion and a rear portion.

19. A microkeratome blade assembly as recited in claim 18 wherein said blade further comprises a side which tapers between said front portion to said rear portion.

20. A microkeratome blade assembly as recited in claim 18 wherein said front portion includes a cutting edge, said cutting edge of said front portion of said blade is wider than said rear portion.

21. A microkeratome blade assembly as recited in claim 13 wherein said blade further comprises an aperture, said blade holder secured to said blade at said aperture.

22. A microkeratome blade assembly as recited in claim 21 wherein said blade holder comprises a lock segment structured to extend into said aperture.

23. A microkeratome blade assembly as recited in claim 13 further comprising a handle removably connected to said blade holder.

24. A microkeratome blade assembly to be used with a microkeratome having a cutting head assembly that moves across a positioning ring, the microkeratome blade assembly comprising:
    a blade holder and a cutting blade connected to said blade holder, said cutting blade shaped so as to avoid interference with movement of the cutting head assembly as said cutting blade oscillates and moves across the positioning ring along an arcuate path.

25. A microkeratome blade assembly as recited in claim 24 wherein said blade holder is structured to be operably driven at a top side thereof.

26. A microkeratome blade assembly as recited in claim 24 wherein said blade holder is structured to be operably driven from a generally vertical orientation.

27. A microkeratome blade assembly as recited in claim 24 wherein said blade holder includes a recess structured to receive a pin from a generally vertical orientation.

28. A microkeratome blade assembly as recited in claim 24 wherein said blade comprises a cutting edge, said cutting edge being wider than at least another portion of said blade.

29. A microkeratome blade assembly as recited in claim 24 wherein said blade further comprises at least four edges.

30. A microkeratome blade assembly as recited in claim 24 wherein said blade further comprises a front portion and a rear portion.

31. A microkeratome blade assembly as recited in claim 30 wherein said blade further comprises a side which tapers between said front portion to said rear portion.

32. A microkeratome blade assembly as recited in claim 30 wherein said front portion includes a cutting edge, said cutting edge of said front portion of said blade is wider than said rear portion.

33. A microkeratome blade assembly as recited in claim 24 wherein said blade further comprises an aperture, said blade holder secured to said blade at said aperture.

34. A microkeratome blade assembly as recited in claim 33 wherein said blade holder comprises a lock segment structured to extend into said aperture.

35. A microkeratome blade assembly as recited in claim 24 further comprising a handle removably connected to said blade holder.

36. A microkeratome blade assembly to be used with a microkeratome having a cutting head assembly that moves across a positioning ring, the microkeratome blade assembly comprising:
    a blade holder; and
    a cutting blade connected to said blade holder, said cutting blade shaped to provide clearance from the positioning ring as the microkeratome cutting blade assembly is oscillated such that said cutting blade will not interfere with movement of the cutting head assembly across the positioning ring along an arcuate path.

* * * * *